United States Patent
Mardinly et al.

(10) Patent No.: US 12,421,529 B2
(45) Date of Patent: Sep. 23, 2025

(54) MODULAR GENETICALLY ENGINEERED CELL AND METHODS OF GENERATION THEREOF

(71) Applicant: Science Corporation, Alameda, CA (US)

(72) Inventors: Alan Mardinly, Alameda, CA (US); Kevin Smith, Alameda, CA (US); Satoru Miura, Alameda, CA (US)

(73) Assignee: Science Corporation, Alameda, CA (US)

( * ) Notice: Subject to any disclaimer, the term of this patent is extended or adjusted under 35 U.S.C. 154(b) by 0 days.

(21) Appl. No.: 18/662,102

(22) Filed: May 13, 2024

(65) Prior Publication Data

US 2024/0376500 A1 Nov. 14, 2024

Related U.S. Application Data

(60) Provisional application No. 63/465,759, filed on May 11, 2023.

(51) Int. Cl.
| | |
|---|---|
| *C12N 15/85* | (2006.01) |
| *C12N 5/074* | (2010.01) |
| *C12N 9/22* | (2006.01) |
| *C12N 15/11* | (2006.01) |
| *C12N 15/90* | (2006.01) |

(52) U.S. Cl.
CPC .......... *C12N 15/907* (2013.01); *C12N 5/0696* (2013.01); *C12N 9/22* (2013.01); *C12N 15/11* (2013.01); *C12Y 301/22* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2020/0002727 A1 | 1/2020 | Feary et al. | |
| 2023/0159958 A1 | 5/2023 | Jonsson et al. | |

FOREIGN PATENT DOCUMENTS

| | | | | |
|---|---|---|---|---|
| WO | WO-2023076898 A1 | * | 5/2023 | ............ C12N 15/113 |

OTHER PUBLICATIONS

Gaidukov et al. Nucleic Acids Research 46(80):4072-4086, 2018 (Year: 2018).*
Baser et al. Methods 95:3-12 (Year: 2016).*
Fin et al. Cell Reports 22:2227-2235, 2018 (Year: 2018).*
Guo Cell Research, 25: 767-768, 2015 (Year: 2015).*
Dai et al. Molecular Therapy—Nucleic Acids (2016) 5, e349; doi: 10.1038/mtna.2016.58; published online Aug. 16, 2016 (Year: 2016).*
Zhang J Cell Physiol 2021;236;2459-2481 (Year: 2021).*
Lu et al. International Journal of Molecular Sciences, 2022, 23, 9862. https://doi.org/10.3390/ijms23179862, pp. 1-15 (Year: 2022).*
Duportet, Xavier , "Developing new tools and platforms for mammalian synthetic biology: From the assembly and chromosomal integration of complex DNA circuits to the engineering of artificial intercellular communication systems", HAL Id: tel-01108520, https://theses.hal.science/tel-01108520, Submitted on Jan. 22, 2015.
Merrick, C. A. , et al., "Rapid Optimization of Engineered Metabolic Pathways with Serine Integrase Recombinational Assembly (SIRA)", Methods in Enzymology, vol. 575, Mar. 23, 2016, ISSN 0076-6879, http://dx.doi.org/10.1016/bs.mie.2016.02.009.
Rosenstein, Aaron H., et al., "A Flexible Transgene Integration 'Landing-Pad' Toolkit in Human Induced Pluripotent Stem Cells Enables Facile Cellular Engineering, Gene Zygosity Control, and Parallel Transgene Integration", bioRxiv, https://doi.org/10.1101/2023.03.03.531057, Mar. 4, 2023.
Yarnall, Matthew T. N., et al., "Drag-and-drop genome insertion of large sequences without double-strand DNA cleavage using CRISPR-directed integrases", Nature Biotechnology, https://doi.org/10.1038/s41587-022-01527-4, published Nov. 24, 2022.
Fatma, et al., "A landing pad system for multicopy gene integration in Issatchenkia orientalis", 1-22. Metabolic Engineering. May 21, 2023. doi: https://doi.org/10.1101/2023.05.21.541627.
Nand , et al., "Genetic and spatial organization of the unusual chromosomes of the dinoflagellate Symbiodinium microadriaticum", pp. 618-629. Nature Genetics. Apr. 29, 2021. p. 622; https://doi.org/10.1038/s41588-021-00841-y.
Pellenz, Stefan , et al., "New Human Chromosomal Sites with "Safe Harbor" Potential for Targeted Transgene Insertion", 814-828, Human Gene Therapy. DOI: 10.1089/hum.2018.169 . Jul. 16, 2019.

* cited by examiner

*Primary Examiner* — Marcia S Noble
(74) *Attorney, Agent, or Firm* — Jeffrey Schox; Annabel Imbrie-Moore

(57) ABSTRACT

In variants, the method for generating a modular cell can include: integrating a landing site into a cell genome, and integrating a gene of interest into the landing site. The method can optionally include performing a cell selection, removing the gene of interest from the landing site, and/or any other suitable steps.

7 Claims, 23 Drawing Sheets

Specification includes a Sequence Listing.

SEQUENCE LISTING

```
Sequence total quantity: 156
SEQ ID NO: 1            moltype = DNA  length = 46
FEATURE                 Location/Qualifiers
source                  1..46
                        mol_type = other DNA
                        organism = synthetic construct
SEQUENCE: 1
gtgcgggtgc cagggcgtgc ccacgggctc cccgggcgcg tactcc            46

SEQ ID NO: 2            moltype = DNA  length = 46
FEATURE                 Location/Qualifiers
source                  1..46
                        mol_type = other DNA
                        organism = synthetic construct
SEQUENCE: 2
gtgcgggtgc cagggcgtgc ccaggggctc cccgggcgcg tactcc            46

SEQ ID NO: 3            moltype = DNA  length = 46
FEATURE                 Location/Qualifiers
source                  1..46
                        mol_type = other DNA
                        organism = synthetic construct
SEQUENCE: 3
gtgcgggtgc cagggcgtgc ccccgggctc cccgggcgcg tactcc            46

SEQ ID NO: 4            moltype = DNA  length = 46
FEATURE                 Location/Qualifiers
source                  1..46
                        mol_type = other DNA
                        organism = synthetic construct
SEQUENCE: 4
gtgcgggtgc cagggcgtgc cctcgggctc cccgggcgcg tactcc            46

SEQ ID NO: 5            moltype = DNA  length = 46
FEATURE                 Location/Qualifiers
source                  1..46
                        mol_type = other DNA
                        organism = synthetic construct
SEQUENCE: 5
gtgcgggtgc cagggcgtgc cctggggctc cccgggcgcg tactcc            46

SEQ ID NO: 6            moltype = DNA  length = 46
```

```
FEATURE              Location/Qualifiers
source               1..46
                     mol_type = other DNA
                     organism = synthetic construct
SEQUENCE: 6
gtgcgggtgc cagggcgtgc ccttgggctc cccgggcgcg tactcc              46

SEQ ID NO: 7         moltype = DNA  length = 38
FEATURE              Location/Qualifiers
source               1..38
                     mol_type = other DNA
                     organism = synthetic construct
SEQUENCE: 7
ggcttgtcga cgacggcgac ctccgtcgtc aggatcat                       38

SEQ ID NO: 8         moltype = DNA  length = 38
FEATURE              Location/Qualifiers
source               1..38
                     mol_type = other DNA
                     organism = synthetic construct
SEQUENCE: 8
ggcttgtcga cgacggcgag ctccgtcgtc aggatcat                       38

SEQ ID NO: 9         moltype = DNA  length = 38
FEATURE              Location/Qualifiers
source               1..38
                     mol_type = other DNA
                     organism = synthetic construct
SEQUENCE: 9
ggcttgtcga cgacggcgcc ctccgtcgtc aggatcat                       38

SEQ ID NO: 10        moltype = DNA  length = 38
FEATURE              Location/Qualifiers
source               1..38
                     mol_type = other DNA
                     organism = synthetic construct
SEQUENCE: 10
ggcttgtcga cgacggcgtc ctccgtcgtc aggatcat                       38

SEQ ID NO: 11        moltype = DNA  length = 38
FEATURE              Location/Qualifiers
source               1..38
                     mol_type = other DNA
                     organism = synthetic construct
SEQUENCE: 11
ggcttgtcga cgacggcgtg ctccgtcgtc aggatcat                       38

SEQ ID NO: 12        moltype = DNA  length = 38
FEATURE              Location/Qualifiers
source               1..38
                     mol_type = other DNA
                     organism = synthetic construct
SEQUENCE: 12
ggcttgtcga cgacggcgtt ctccgtcgtc aggatcat                       38

SEQ ID NO: 13        moltype = DNA  length = 44
FEATURE              Location/Qualifiers
source               1..44
                     mol_type = other DNA
                     organism = synthetic construct
SEQUENCE: 13
gcggtctcca tcgggatctg cacatcgagc agcatgccga ccag                44

SEQ ID NO: 14        moltype = DNA  length = 44
FEATURE              Location/Qualifiers
source               1..44
                     mol_type = other DNA
                     organism = synthetic construct
SEQUENCE: 14
gcggtctcca tcgggatctg cagatcgagc agcatgccga ccag                44

SEQ ID NO: 15        moltype = DNA  length = 44
FEATURE              Location/Qualifiers
source               1..44
                     mol_type = other DNA
                     organism = synthetic construct
SEQUENCE: 15
gcggtctcca tcgggatctg cccatcgagc agcatgccga ccag                44
```

```
SEQ ID NO: 16            moltype = DNA   length = 44
FEATURE                  Location/Qualifiers
source                   1..44
                         mol_type = other DNA
                         organism = synthetic construct
SEQUENCE: 16
gcggtctcca tcgggatctg ctcatcgagc agcatgccga ccag                 44

SEQ ID NO: 17            moltype = DNA   length = 44
FEATURE                  Location/Qualifiers
source                   1..44
                         mol_type = other DNA
                         organism = synthetic construct
SEQUENCE: 17
gcggtctcca tcgggatctg ctgatcgagc agcatgccga ccag                 44

SEQ ID NO: 18            moltype = DNA   length = 44
FEATURE                  Location/Qualifiers
source                   1..44
                         mol_type = other DNA
                         organism = synthetic construct
SEQUENCE: 18
gcggtctcca tcgggatctg cttatcgagc agcatgccga ccag                 44

SEQ ID NO: 19            moltype = DNA   length = 50
FEATURE                  Location/Qualifiers
source                   1..50
                         mol_type = other DNA
                         organism = synthetic construct
SEQUENCE: 19
cagtgggtga acgcaaagat ggggacctcg atgccgagct cgtcgcagag           50

SEQ ID NO: 20            moltype = DNA   length = 50
FEATURE                  Location/Qualifiers
source                   1..50
                         mol_type = other DNA
                         organism = synthetic construct
SEQUENCE: 20
cagtgggtga acgcaaagat ggggagctcg atgccgagct cgtcgcagag           50

SEQ ID NO: 21            moltype = DNA   length = 50
FEATURE                  Location/Qualifiers
source                   1..50
                         mol_type = other DNA
                         organism = synthetic construct
SEQUENCE: 21
cagtgggtga acgcaaagat ggggccctcg atgccgagct cgtcgcagag           50

SEQ ID NO: 22            moltype = DNA   length = 50
FEATURE                  Location/Qualifiers
source                   1..50
                         mol_type = other DNA
                         organism = synthetic construct
SEQUENCE: 22
cagtgggtga acgcaaagat ggggtcctcg atgccgagct cgtcgcagag           50

SEQ ID NO: 23            moltype = DNA   length = 50
FEATURE                  Location/Qualifiers
source                   1..50
                         mol_type = other DNA
                         organism = synthetic construct
SEQUENCE: 23
cagtgggtga acgcaaagat ggggtgctcg atgccgagct cgtcgcagag           50

SEQ ID NO: 24            moltype = DNA   length = 50
FEATURE                  Location/Qualifiers
source                   1..50
                         mol_type = other DNA
                         organism = synthetic construct
SEQUENCE: 24
cagtgggtga acgcaaagat ggggttctcg atgccgagct cgtcgcagag           50

SEQ ID NO: 25            moltype = DNA   length = 48
FEATURE                  Location/Qualifiers
source                   1..48
                         mol_type = other DNA
                         organism = synthetic construct
SEQUENCE: 25
cggtattcgg cgcgatccgc ggcacgaaga acatcaccct gaacatcg             48
```

```
SEQ ID NO: 26          moltype = DNA  length = 48
FEATURE                Location/Qualifiers
source                 1..48
                       mol_type = other DNA
                       organism = synthetic construct
SEQUENCE: 26
cggtattcgg cgcgatccgc ggcaggaaga acatcaccct gaacatcg              48

SEQ ID NO: 27          moltype = DNA  length = 48
FEATURE                Location/Qualifiers
source                 1..48
                       mol_type = other DNA
                       organism = synthetic construct
SEQUENCE: 27
cggtattcgg cgcgatccgc ggcccgaaga acatcaccct gaacatcg              48

SEQ ID NO: 28          moltype = DNA  length = 48
FEATURE                Location/Qualifiers
source                 1..48
                       mol_type = other DNA
                       organism = synthetic construct
SEQUENCE: 28
cggtattcgg cgcgatccgc ggctcgaaga acatcaccct gaacatcg              48

SEQ ID NO: 29          moltype = DNA  length = 48
FEATURE                Location/Qualifiers
source                 1..48
                       mol_type = other DNA
                       organism = synthetic construct
SEQUENCE: 29
cggtattcgg cgcgatccgc ggctggaaga acatcaccct gaacatcg              48

SEQ ID NO: 30          moltype = DNA  length = 48
FEATURE                Location/Qualifiers
source                 1..48
                       mol_type = other DNA
                       organism = synthetic construct
SEQUENCE: 30
cggtattcgg cgcgatccgc ggcttgaaga acatcaccct gaacatcg              48

SEQ ID NO: 31          moltype = DNA  length = 42
FEATURE                Location/Qualifiers
source                 1..42
                       mol_type = other DNA
                       organism = synthetic construct
SEQUENCE: 31
gtgccccaac tggggtaacc tacgagttct ctcagttggg gg                    42

SEQ ID NO: 32          moltype = DNA  length = 42
FEATURE                Location/Qualifiers
source                 1..42
                       mol_type = other DNA
                       organism = synthetic construct
SEQUENCE: 32
gtgccccaac tggggtaacc taggagttct ctcagttggg gg                    42

SEQ ID NO: 33          moltype = DNA  length = 42
FEATURE                Location/Qualifiers
source                 1..42
                       mol_type = other DNA
                       organism = synthetic construct
SEQUENCE: 33
gtgccccaac tggggtaacc tccgagttct ctcagttggg gg                    42

SEQ ID NO: 34          moltype = DNA  length = 42
FEATURE                Location/Qualifiers
source                 1..42
                       mol_type = other DNA
                       organism = synthetic construct
SEQUENCE: 34
gtgccccaac tggggtaacc ttcgagttct ctcagttggg gg                    42

SEQ ID NO: 35          moltype = DNA  length = 42
FEATURE                Location/Qualifiers
source                 1..42
                       mol_type = other DNA
                       organism = synthetic construct
SEQUENCE: 35
```

```
gtgccccaac tggggtaacc ttggagttct ctcagttggg gg                           42

SEQ ID NO: 36          moltype = DNA   length = 42
FEATURE                Location/Qualifiers
source                 1..42
                       mol_type = other DNA
                       organism = synthetic construct
SEQUENCE: 36
gtgccccaac tggggtaacc tttgagttct ctcagttggg gg                           42

SEQ ID NO: 37          moltype = DNA   length = 52
FEATURE                Location/Qualifiers
source                 1..52
                       mol_type = other DNA
                       organism = synthetic construct
SEQUENCE: 37
gtggtttgtc tggtcaacca ccgcgacctc agtggtgtac ggtacaaacc ca                52

SEQ ID NO: 38          moltype = DNA   length = 52
FEATURE                Location/Qualifiers
source                 1..52
                       mol_type = other DNA
                       organism = synthetic construct
SEQUENCE: 38
gtggtttgtc tggtcaacca ccgcgagctc agtggtgtac ggtacaaacc ca                52

SEQ ID NO: 39          moltype = DNA   length = 52
FEATURE                Location/Qualifiers
source                 1..52
                       mol_type = other DNA
                       organism = synthetic construct
SEQUENCE: 39
gtggtttgtc tggtcaacca ccgcgccctc agtggtgtac ggtacaaacc ca                52

SEQ ID NO: 40          moltype = DNA   length = 52
FEATURE                Location/Qualifiers
source                 1..52
                       mol_type = other DNA
                       organism = synthetic construct
SEQUENCE: 40
gtggtttgtc tggtcaacca ccgcgtcctc agtggtgtac ggtacaaacc ca                52

SEQ ID NO: 41          moltype = DNA   length = 52
FEATURE                Location/Qualifiers
source                 1..52
                       mol_type = other DNA
                       organism = synthetic construct
SEQUENCE: 41
gtggtttgtc tggtcaacca ccgcgtgctc agtggtgtac ggtacaaacc ca                52

SEQ ID NO: 42          moltype = DNA   length = 52
FEATURE                Location/Qualifiers
source                 1..52
                       mol_type = other DNA
                       organism = synthetic construct
SEQUENCE: 42
gtggtttgtc tggtcaacca ccgcgttctc agtggtgtac ggtacaaacc ca                52

SEQ ID NO: 43          moltype = DNA   length = 52
FEATURE                Location/Qualifiers
source                 1..52
                       mol_type = other DNA
                       organism = synthetic construct
SEQUENCE: 43
tagtttccaa tgttacagga actgcacgca gaatccaaca cattggaagt cg                52

SEQ ID NO: 44          moltype = DNA   length = 52
FEATURE                Location/Qualifiers
source                 1..52
                       mol_type = other DNA
                       organism = synthetic construct
SEQUENCE: 44
tagtttccaa tgttacagga actgcaggca gaatccaaca cattggaagt cg                52

SEQ ID NO: 45          moltype = DNA   length = 52
FEATURE                Location/Qualifiers
source                 1..52
                       mol_type = other DNA
                       organism = synthetic construct
```

```
SEQUENCE: 45
tagtttccaa tgttacagga actgcccgca gaatccaaca cattggaagt cg          52

SEQ ID NO: 46           moltype = DNA   length = 52
FEATURE                 Location/Qualifiers
source                  1..52
                        mol_type = other DNA
                        organism = synthetic construct
SEQUENCE: 46
tagtttccaa tgttacagga actgctcgca gaatccaaca cattggaagt cg          52

SEQ ID NO: 47           moltype = DNA   length = 52
FEATURE                 Location/Qualifiers
source                  1..52
                        mol_type = other DNA
                        organism = synthetic construct
SEQUENCE: 47
tagtttccaa tgttacagga actgctggca gaatccaaca cattggaagt cg          52

SEQ ID NO: 48           moltype = DNA   length = 52
FEATURE                 Location/Qualifiers
source                  1..52
                        mol_type = other DNA
                        organism = synthetic construct
SEQUENCE: 48
tagtttccaa tgttacagga actgcttgca gaatccaaca cattggaagt cg          52

SEQ ID NO: 49           moltype = DNA   length = 46
FEATURE                 Location/Qualifiers
source                  1..46
                        mol_type = other DNA
                        organism = synthetic construct
SEQUENCE: 49
ttgtcaaagt ctaaagatgg ggacctcaat attcatgctt tgcgaa                46

SEQ ID NO: 50           moltype = DNA   length = 46
FEATURE                 Location/Qualifiers
source                  1..46
                        mol_type = other DNA
                        organism = synthetic construct
SEQUENCE: 50
ttgtcaaagt ctaaagatgg ggagctcaat attcatgctt tgcgaa                46

SEQ ID NO: 51           moltype = DNA   length = 46
FEATURE                 Location/Qualifiers
source                  1..46
                        mol_type = other DNA
                        organism = synthetic construct
SEQUENCE: 51
ttgtcaaagt ctaaagatgg ggccctcaat attcatgctt tgcgaa                46

SEQ ID NO: 52           moltype = DNA   length = 46
FEATURE                 Location/Qualifiers
source                  1..46
                        mol_type = other DNA
                        organism = synthetic construct
SEQUENCE: 52
ttgtcaaagt ctaaagatgg ggtcctcaat attcatgctt tgcgaa                46

SEQ ID NO: 53           moltype = DNA   length = 46
FEATURE                 Location/Qualifiers
source                  1..46
                        mol_type = other DNA
                        organism = synthetic construct
SEQUENCE: 53
ttgtcaaagt ctaaagatgg ggtgctcaat attcatgctt tgcgaa                46

SEQ ID NO: 54           moltype = DNA   length = 46
FEATURE                 Location/Qualifiers
source                  1..46
                        mol_type = other DNA
                        organism = synthetic construct
SEQUENCE: 54
ttgtcaaagt ctaaagatgg ggttctcaat attcatgctt tgcgaa                46

SEQ ID NO: 55           moltype = DNA   length = 46
FEATURE                 Location/Qualifiers
source                  1..46
                        mol_type = other DNA
```

```
                    organism = synthetic construct
SEQUENCE: 55
ttcgcaaagc ctcaaaatcg ggacctcgat attcatgctt tgtgaa              46

SEQ ID NO: 56           moltype = DNA  length = 46
FEATURE                 Location/Qualifiers
source                  1..46
                        mol_type = other DNA
                        organism = synthetic construct
SEQUENCE: 56
ttcgcaaagc ctcaaaatcg ggagctcgat attcatgctt tgtgaa              46

SEQ ID NO: 57           moltype = DNA  length = 46
FEATURE                 Location/Qualifiers
source                  1..46
                        mol_type = other DNA
                        organism = synthetic construct
SEQUENCE: 57
ttcgcaaagc ctcaaaatcg ggccctcgat attcatgctt tgtgaa              46

SEQ ID NO: 58           moltype = DNA  length = 46
FEATURE                 Location/Qualifiers
source                  1..46
                        mol_type = other DNA
                        organism = synthetic construct
SEQUENCE: 58
ttcgcaaagc ctcaaaatcg ggtcctcgat attcatgctt tgtgaa              46

SEQ ID NO: 59           moltype = DNA  length = 46
FEATURE                 Location/Qualifiers
source                  1..46
                        mol_type = other DNA
                        organism = synthetic construct
SEQUENCE: 59
ttcgcaaagc ctcaaaatcg ggtgctcgat attcatgctt tgtgaa              46

SEQ ID NO: 60           moltype = DNA  length = 46
FEATURE                 Location/Qualifiers
source                  1..46
                        mol_type = other DNA
                        organism = synthetic construct
SEQUENCE: 60
ttcgcaaagc ctcaaaatcg ggttctcgat attcatgctt tgtgaa              46

SEQ ID NO: 61           moltype = DNA  length = 52
FEATURE                 Location/Qualifiers
source                  1..52
                        mol_type = other DNA
                        organism = synthetic construct
SEQUENCE: 61
cctttcgggg gatgtgatgt tcgagacgaa gaacatcacc ctgaacatcg cg       52

SEQ ID NO: 62           moltype = DNA  length = 52
FEATURE                 Location/Qualifiers
source                  1..52
                        mol_type = other DNA
                        organism = synthetic construct
SEQUENCE: 62
cctttcgggg gatgtgatgt tcgagaggaa gaacatcacc ctgaacatcg cg       52

SEQ ID NO: 63           moltype = DNA  length = 52
FEATURE                 Location/Qualifiers
source                  1..52
                        mol_type = other DNA
                        organism = synthetic construct
SEQUENCE: 63
cctttcgggg gatgtgatgt tcgagccgaa gaacatcacc ctgaacatcg cg       52

SEQ ID NO: 64           moltype = DNA  length = 52
FEATURE                 Location/Qualifiers
source                  1..52
                        mol_type = other DNA
                        organism = synthetic construct
SEQUENCE: 64
cctttcgggg gatgtgatgt tcgagtcgaa gaacatcacc ctgaacatcg cg       52

SEQ ID NO: 65           moltype = DNA  length = 52
FEATURE                 Location/Qualifiers
source                  1..52
```

```
                                                        -continued
                          mol_type = other DNA
                          organism = synthetic construct
SEQUENCE: 65
cctttcgggg gatgtgatgt tcgagtggaa gaacatcacc ctgaacatcg cg          52

SEQ ID NO: 66             moltype = DNA   length = 52
FEATURE                   Location/Qualifiers
source                    1..52
                          mol_type = other DNA
                          organism = synthetic construct
SEQUENCE: 66
cctttcgggg gatgtgatgt tcgagttgaa gaacatcacc ctgaacatcg cg          52

SEQ ID NO: 67             moltype = DNA   length = 52
FEATURE                   Location/Qualifiers
source                    1..52
                          mol_type = other DNA
                          organism = synthetic construct
SEQUENCE: 67
gtattgggggg aacgcgatat tcgagacgta gaacatcacc ttcaccaaat tc         52

SEQ ID NO: 68             moltype = DNA   length = 52
FEATURE                   Location/Qualifiers
source                    1..52
                          mol_type = other DNA
                          organism = synthetic construct
SEQUENCE: 68
gtattgggggg aacgcgatat tcgagaggta gaacatcacc ttcaccaaat tc         52

SEQ ID NO: 69             moltype = DNA   length = 52
FEATURE                   Location/Qualifiers
source                    1..52
                          mol_type = other DNA
                          organism = synthetic construct
SEQUENCE: 69
gtattgggggg aacgcgatat tcgagccgta gaacatcacc ttcaccaaat tc         52

SEQ ID NO: 70             moltype = DNA   length = 52
FEATURE                   Location/Qualifiers
source                    1..52
                          mol_type = other DNA
                          organism = synthetic construct
SEQUENCE: 70
gtattgggggg aacgcgatat tcgagtcgta gaacatcacc ttcaccaaat tc         52

SEQ ID NO: 71             moltype = DNA   length = 52
FEATURE                   Location/Qualifiers
source                    1..52
                          mol_type = other DNA
                          organism = synthetic construct
SEQUENCE: 71
gtattgggggg aacgcgatat tcgagtggta gaacatcacc ttcaccaaat tc         52

SEQ ID NO: 72             moltype = DNA   length = 52
FEATURE                   Location/Qualifiers
source                    1..52
                          mol_type = other DNA
                          organism = synthetic construct
SEQUENCE: 72
gtattgggggg aacgcgatat tcgagttgta gaacatcacc ttcaccaaat tc         52

SEQ ID NO: 73             moltype = DNA   length = 43
FEATURE                   Location/Qualifiers
source                    1..43
                          mol_type = other DNA
                          organism = synthetic construct
SEQUENCE: 73
gtgcgggtgc cagggcgtgc ccacgagttc tctcagttgg ggg                    43

SEQ ID NO: 74             moltype = DNA   length = 43
FEATURE                   Location/Qualifiers
source                    1..43
                          mol_type = other DNA
                          organism = synthetic construct
SEQUENCE: 74
gtgcgggtgc cagggcgtgc ccaggagttc tctcagttgg ggg                    43

SEQ ID NO: 75             moltype = DNA   length = 43
FEATURE                   Location/Qualifiers
```

```
source                   1..43
                         mol_type = other DNA
                         organism = synthetic construct
SEQUENCE: 75
gtgcgggtgc cagggcgtgc ccccgagttc tctcagttgg ggg              43

SEQ ID NO: 76            moltype = DNA   length = 43
FEATURE                  Location/Qualifiers
source                   1..43
                         mol_type = other DNA
                         organism = synthetic construct
SEQUENCE: 76
gtgcgggtgc cagggcgtgc cctcgagttc tctcagttgg ggg              43

SEQ ID NO: 77            moltype = DNA   length = 43
FEATURE                  Location/Qualifiers
source                   1..43
                         mol_type = other DNA
                         organism = synthetic construct
SEQUENCE: 77
gtgcgggtgc cagggcgtgc cctggagttc tctcagttgg ggg              43

SEQ ID NO: 78            moltype = DNA   length = 43
FEATURE                  Location/Qualifiers
source                   1..43
                         mol_type = other DNA
                         organism = synthetic construct
SEQUENCE: 78
gtgcgggtgc cagggcgtgc ccttgagttc tctcagttgg ggg              43

SEQ ID NO: 79            moltype = DNA   length = 45
FEATURE                  Location/Qualifiers
source                   1..45
                         mol_type = other DNA
                         organism = synthetic construct
SEQUENCE: 79
ggcttgtcga cgacggcgac ctcagtggtg tacggtacaa accca            45

SEQ ID NO: 80            moltype = DNA   length = 45
FEATURE                  Location/Qualifiers
source                   1..45
                         mol_type = other DNA
                         organism = synthetic construct
SEQUENCE: 80
ggcttgtcga cgacggcgag ctcagtggtg tacggtacaa accca            45

SEQ ID NO: 81            moltype = DNA   length = 45
FEATURE                  Location/Qualifiers
source                   1..45
                         mol_type = other DNA
                         organism = synthetic construct
SEQUENCE: 81
ggcttgtcga cgacggcgcc ctcagtggtg tacggtacaa accca             45

SEQ ID NO: 82            moltype = DNA   length = 45
FEATURE                  Location/Qualifiers
source                   1..45
                         mol_type = other DNA
                         organism = synthetic construct
SEQUENCE: 82
ggcttgtcga cgacggcgtc ctcagtggtg tacggtacaa accca             45

SEQ ID NO: 83            moltype = DNA   length = 45
FEATURE                  Location/Qualifiers
source                   1..45
                         mol_type = other DNA
                         organism = synthetic construct
SEQUENCE: 83
ggcttgtcga cgacggcgtg ctcagtggtg tacggtacaa accca             45

SEQ ID NO: 84            moltype = DNA   length = 45
FEATURE                  Location/Qualifiers
source                   1..45
                         mol_type = other DNA
                         organism = synthetic construct
SEQUENCE: 84
ggcttgtcga cgacggcgtt ctcagtggtg tacggtacaa accca             45

SEQ ID NO: 85            moltype = DNA   length = 48
```

```
FEATURE                 Location/Qualifiers
source                  1..48
                        mol_type = other DNA
                        organism = synthetic construct
SEQUENCE: 85
gcggtctcca tcgggatctg cacgcagaat ccaacacatt ggaagtcg            48

SEQ ID NO: 86           moltype = DNA  length = 48
FEATURE                 Location/Qualifiers
source                  1..48
                        mol_type = other DNA
                        organism = synthetic construct
SEQUENCE: 86
gcggtctcca tcgggatctg caggcagaat ccaacacatt ggaagtcg            48

SEQ ID NO: 87           moltype = DNA  length = 48
FEATURE                 Location/Qualifiers
source                  1..48
                        mol_type = other DNA
                        organism = synthetic construct
SEQUENCE: 87
gcggtctcca tcgggatctg cccgcagaat ccaacacatt ggaagtcg            48

SEQ ID NO: 88           moltype = DNA  length = 48
FEATURE                 Location/Qualifiers
source                  1..48
                        mol_type = other DNA
                        organism = synthetic construct
SEQUENCE: 88
gcggtctcca tcgggatctg ctcgcagaat ccaacacatt ggaagtcg            48

SEQ ID NO: 89           moltype = DNA  length = 48
FEATURE                 Location/Qualifiers
source                  1..48
                        mol_type = other DNA
                        organism = synthetic construct
SEQUENCE: 89
gcggtctcca tcgggatctg ctggcagaat ccaacacatt ggaagtcg            48

SEQ ID NO: 90           moltype = DNA  length = 48
FEATURE                 Location/Qualifiers
source                  1..48
                        mol_type = other DNA
                        organism = synthetic construct
SEQUENCE: 90
gcggtctcca tcgggatctg cttgcagaat ccaacacatt ggaagtcg            48

SEQ ID NO: 91           moltype = DNA  length = 48
FEATURE                 Location/Qualifiers
source                  1..48
                        mol_type = other DNA
                        organism = synthetic construct
SEQUENCE: 91
cagtgggtga acgcaaagat ggggacctca atattcatgc tttgcgaa            48

SEQ ID NO: 92           moltype = DNA  length = 48
FEATURE                 Location/Qualifiers
source                  1..48
                        mol_type = other DNA
                        organism = synthetic construct
SEQUENCE: 92
cagtgggtga acgcaaagat ggggagctca atattcatgc tttgcgaa            48

SEQ ID NO: 93           moltype = DNA  length = 48
FEATURE                 Location/Qualifiers
source                  1..48
                        mol_type = other DNA
                        organism = synthetic construct
SEQUENCE: 93
cagtgggtga acgcaaagat ggggccctca atattcatgc tttgcgaa            48

SEQ ID NO: 94           moltype = DNA  length = 48
FEATURE                 Location/Qualifiers
source                  1..48
                        mol_type = other DNA
                        organism = synthetic construct
SEQUENCE: 94
cagtgggtga acgcaaagat ggggtcctca atattcatgc tttgcgaa            48
```

-continued

```
SEQ ID NO: 95         moltype = DNA   length = 48
FEATURE               Location/Qualifiers
source                1..48
                      mol_type = other DNA
                      organism = synthetic construct
SEQUENCE: 95
cagtgggtga acgcaaagat ggggtgctca atattcatgc tttgcgaa                    48

SEQ ID NO: 96         moltype = DNA   length = 48
FEATURE               Location/Qualifiers
source                1..48
                      mol_type = other DNA
                      organism = synthetic construct
SEQUENCE: 96
cagtgggtga acgcaaagat ggggttctca atattcatgc tttgcgaa                    48

SEQ ID NO: 97         moltype = DNA   length = 48
FEATURE               Location/Qualifiers
source                1..48
                      mol_type = other DNA
                      organism = synthetic construct
SEQUENCE: 97
cagtgggtga acgcaaagat ggggacctcg atattcatgc tttgtgaa                    48

SEQ ID NO: 98         moltype = DNA   length = 48
FEATURE               Location/Qualifiers
source                1..48
                      mol_type = other DNA
                      organism = synthetic construct
SEQUENCE: 98
cagtgggtga acgcaaagat ggggagctcg atattcatgc tttgtgaa                    48

SEQ ID NO: 99         moltype = DNA   length = 48
FEATURE               Location/Qualifiers
source                1..48
                      mol_type = other DNA
                      organism = synthetic construct
SEQUENCE: 99
cagtgggtga acgcaaagat ggggccctcg atattcatgc tttgtgaa                    48

SEQ ID NO: 100        moltype = DNA   length = 48
FEATURE               Location/Qualifiers
source                1..48
                      mol_type = other DNA
                      organism = synthetic construct
SEQUENCE: 100
cagtgggtga acgcaaagat ggggtcctcg atattcatgc tttgtgaa                    48

SEQ ID NO: 101        moltype = DNA   length = 48
FEATURE               Location/Qualifiers
source                1..48
                      mol_type = other DNA
                      organism = synthetic construct
SEQUENCE: 101
cagtgggtga acgcaaagat ggggtgctcg atattcatgc tttgtgaa                    48

SEQ ID NO: 102        moltype = DNA   length = 48
FEATURE               Location/Qualifiers
source                1..48
                      mol_type = other DNA
                      organism = synthetic construct
SEQUENCE: 102
cagtgggtga acgcaaagat ggggttctcg atattcatgc tttgtgaa                    48

SEQ ID NO: 103        moltype = DNA   length = 50
FEATURE               Location/Qualifiers
source                1..50
                      mol_type = other DNA
                      organism = synthetic construct
SEQUENCE: 103
cggtattcgg cgcgatccgc ggcacgaaga acatcaccct gaacatcgcg                  50

SEQ ID NO: 104        moltype = DNA   length = 50
FEATURE               Location/Qualifiers
source                1..50
                      mol_type = other DNA
                      organism = synthetic construct
SEQUENCE: 104
cggtattcgg cgcgatccgc ggcaggaaga acatcaccct gaacatcgcg                  50
```

```
SEQ ID NO: 105         moltype = DNA   length = 50
FEATURE                Location/Qualifiers
source                 1..50
                       mol_type = other DNA
                       organism = synthetic construct
SEQUENCE: 105
cggtattcgg cgcgatccgc ggcccgaaga acatcaccct gaacatcgcg              50

SEQ ID NO: 106         moltype = DNA   length = 50
FEATURE                Location/Qualifiers
source                 1..50
                       mol_type = other DNA
                       organism = synthetic construct
SEQUENCE: 106
cggtattcgg cgcgatccgc ggctcgaaga acatcaccct gaacatcgcg              50

SEQ ID NO: 107         moltype = DNA   length = 50
FEATURE                Location/Qualifiers
source                 1..50
                       mol_type = other DNA
                       organism = synthetic construct
SEQUENCE: 107
cggtattcgg cgcgatccgc ggctggaaga acatcaccct gaacatcgcg              50

SEQ ID NO: 108         moltype = DNA   length = 50
FEATURE                Location/Qualifiers
source                 1..50
                       mol_type = other DNA
                       organism = synthetic construct
SEQUENCE: 108
cggtattcgg cgcgatccgc ggcttgaaga acatcaccct gaacatcgcg              50

SEQ ID NO: 109         moltype = DNA   length = 50
FEATURE                Location/Qualifiers
source                 1..50
                       mol_type = other DNA
                       organism = synthetic construct
SEQUENCE: 109
cggtattcgg cgcgatccgc ggcacgtaga acatcacctt caccaaattc              50

SEQ ID NO: 110         moltype = DNA   length = 50
FEATURE                Location/Qualifiers
source                 1..50
                       mol_type = other DNA
                       organism = synthetic construct
SEQUENCE: 110
cggtattcgg cgcgatccgc ggcaggtaga acatcacctt caccaaattc              50

SEQ ID NO: 111         moltype = DNA   length = 50
FEATURE                Location/Qualifiers
source                 1..50
                       mol_type = other DNA
                       organism = synthetic construct
SEQUENCE: 111
cggtattcgg cgcgatccgc ggcccgtaga acatcacctt caccaaattc              50

SEQ ID NO: 112         moltype = DNA   length = 50
FEATURE                Location/Qualifiers
source                 1..50
                       mol_type = other DNA
                       organism = synthetic construct
SEQUENCE: 112
cggtattcgg cgcgatccgc ggctcgtaga acatcacctt caccaaattc              50

SEQ ID NO: 113         moltype = DNA   length = 50
FEATURE                Location/Qualifiers
source                 1..50
                       mol_type = other DNA
                       organism = synthetic construct
SEQUENCE: 113
cggtattcgg cgcgatccgc ggctggtaga acatcacctt caccaaattc              50

SEQ ID NO: 114         moltype = DNA   length = 50
FEATURE                Location/Qualifiers
source                 1..50
                       mol_type = other DNA
                       organism = synthetic construct
SEQUENCE: 114
```

```
cggtattcgg cgcgatccgc ggcttgtaga acatcacctt caccaaattc                          50

SEQ ID NO: 115          moltype = DNA   length = 45
FEATURE                 Location/Qualifiers
source                  1..45
                        mol_type = other DNA
                        organism = synthetic construct
SEQUENCE: 115
gtgccccaac tggggtaacc tacgggctcc ccgggcgcgt actcc                               45

SEQ ID NO: 116          moltype = DNA   length = 45
FEATURE                 Location/Qualifiers
source                  1..45
                        mol_type = other DNA
                        organism = synthetic construct
SEQUENCE: 116
gtgccccaac tggggtaacc tagggctcc ccgggcgcgt actcc                                45

SEQ ID NO: 117          moltype = DNA   length = 45
FEATURE                 Location/Qualifiers
source                  1..45
                        mol_type = other DNA
                        organism = synthetic construct
SEQUENCE: 117
gtgccccaac tggggtaacc tccgggctcc ccgggcgcgt actcc                               45

SEQ ID NO: 118          moltype = DNA   length = 45
FEATURE                 Location/Qualifiers
source                  1..45
                        mol_type = other DNA
                        organism = synthetic construct
SEQUENCE: 118
gtgccccaac tggggtaacc ttcgggctcc ccgggcgcgt actcc                               45

SEQ ID NO: 119          moltype = DNA   length = 45
FEATURE                 Location/Qualifiers
source                  1..45
                        mol_type = other DNA
                        organism = synthetic construct
SEQUENCE: 119
gtgccccaac tggggtaacc ttgggctcc ccgggcgcgt actcc                                45

SEQ ID NO: 120          moltype = DNA   length = 45
FEATURE                 Location/Qualifiers
source                  1..45
                        mol_type = other DNA
                        organism = synthetic construct
SEQUENCE: 120
gtgccccaac tggggtaacc tttgggctcc ccgggcgcgt actcc                               45

SEQ ID NO: 121          moltype = DNA   length = 45
FEATURE                 Location/Qualifiers
source                  1..45
                        mol_type = other DNA
                        organism = synthetic construct
SEQUENCE: 121
gtggtttgtc tggtcaacca ccgcgacctc cgtcgtcagg atcat                               45

SEQ ID NO: 122          moltype = DNA   length = 45
FEATURE                 Location/Qualifiers
source                  1..45
                        mol_type = other DNA
                        organism = synthetic construct
SEQUENCE: 122
gtggtttgtc tggtcaacca ccgcgagctc cgtcgtcagg atcat                               45

SEQ ID NO: 123          moltype = DNA   length = 45
FEATURE                 Location/Qualifiers
source                  1..45
                        mol_type = other DNA
                        organism = synthetic construct
SEQUENCE: 123
gtggtttgtc tggtcaacca ccgcgccctc cgtcgtcagg atcat                               45

SEQ ID NO: 124          moltype = DNA   length = 45
FEATURE                 Location/Qualifiers
source                  1..45
                        mol_type = other DNA
                        organism = synthetic construct
```

-continued

```
SEQUENCE: 124
gtggtttgtc tggtcaacca ccgcgtcctc cgtcgtcagg atcat                45

SEQ ID NO: 125          moltype = DNA   length = 45
FEATURE                 Location/Qualifiers
source                  1..45
                        mol_type = other DNA
                        organism = synthetic construct
SEQUENCE: 125
gtggtttgtc tggtcaacca ccgcgtgctc cgtcgtcagg atcat                45

SEQ ID NO: 126          moltype = DNA   length = 45
FEATURE                 Location/Qualifiers
source                  1..45
                        mol_type = other DNA
                        organism = synthetic construct
SEQUENCE: 126
gtggtttgtc tggtcaacca ccgcgttctc cgtcgtcagg atcat                45

SEQ ID NO: 127          moltype = DNA   length = 48
FEATURE                 Location/Qualifiers
source                  1..48
                        mol_type = other DNA
                        organism = synthetic construct
SEQUENCE: 127
tagtttccaa tgttacagga actgcacatc gagcagcatg ccgaccag             48

SEQ ID NO: 128          moltype = DNA   length = 48
FEATURE                 Location/Qualifiers
source                  1..48
                        mol_type = other DNA
                        organism = synthetic construct
SEQUENCE: 128
tagtttccaa tgttacagga actgcagatc gagcagcatg ccgaccag             48

SEQ ID NO: 129          moltype = DNA   length = 48
FEATURE                 Location/Qualifiers
source                  1..48
                        mol_type = other DNA
                        organism = synthetic construct
SEQUENCE: 129
tagtttccaa tgttacagga actgcccatc gagcagcatg ccgaccag             48

SEQ ID NO: 130          moltype = DNA   length = 48
FEATURE                 Location/Qualifiers
source                  1..48
                        mol_type = other DNA
                        organism = synthetic construct
SEQUENCE: 130
tagtttccaa tgttacagga actgctcatc gagcagcatg ccgaccag             48

SEQ ID NO: 131          moltype = DNA   length = 48
FEATURE                 Location/Qualifiers
source                  1..48
                        mol_type = other DNA
                        organism = synthetic construct
SEQUENCE: 131
tagtttccaa tgttacagga actgctgatc gagcagcatg ccgaccag             48

SEQ ID NO: 132          moltype = DNA   length = 48
FEATURE                 Location/Qualifiers
source                  1..48
                        mol_type = other DNA
                        organism = synthetic construct
SEQUENCE: 132
tagtttccaa tgttacagga actgcttatc gagcagcatg ccgaccag             48

SEQ ID NO: 133          moltype = DNA   length = 48
FEATURE                 Location/Qualifiers
source                  1..48
                        mol_type = other DNA
                        organism = synthetic construct
SEQUENCE: 133
ttgtcaaagt ctaaagatgg ggacctcgat gccgagctcg tcgcagag             48

SEQ ID NO: 134          moltype = DNA   length = 48
FEATURE                 Location/Qualifiers
source                  1..48
                        mol_type = other DNA
```

```
                              -continued
                              organism = synthetic construct
SEQUENCE: 134
ttgtcaaagt ctaaagatgg ggagctcgat gccgagctcg tcgcagag              48

SEQ ID NO: 135        moltype = DNA   length = 48
FEATURE               Location/Qualifiers
source                1..48
                      mol_type = other DNA
                      organism = synthetic construct
SEQUENCE: 135
ttgtcaaagt ctaaagatgg ggccctcgat gccgagctcg tcgcagag              48

SEQ ID NO: 136        moltype = DNA   length = 48
FEATURE               Location/Qualifiers
source                1..48
                      mol_type = other DNA
                      organism = synthetic construct
SEQUENCE: 136
ttgtcaaagt ctaaagatgg ggtcctcgat gccgagctcg tcgcagag              48

SEQ ID NO: 137        moltype = DNA   length = 48
FEATURE               Location/Qualifiers
source                1..48
                      mol_type = other DNA
                      organism = synthetic construct
SEQUENCE: 137
ttgtcaaagt ctaaagatgg ggtgctcgat gccgagctcg tcgcagag              48

SEQ ID NO: 138        moltype = DNA   length = 48
FEATURE               Location/Qualifiers
source                1..48
                      mol_type = other DNA
                      organism = synthetic construct
SEQUENCE: 138
ttgtcaaagt ctaaagatgg ggttctcgat gccgagctcg tcgcagag              48

SEQ ID NO: 139        moltype = DNA   length = 48
FEATURE               Location/Qualifiers
source                1..48
                      mol_type = other DNA
                      organism = synthetic construct
SEQUENCE: 139
ttcgcaaagc ctcaaaatcg ggacctcgat gccgagctcg tcgcagag              48

SEQ ID NO: 140        moltype = DNA   length = 48
FEATURE               Location/Qualifiers
source                1..48
                      mol_type = other DNA
                      organism = synthetic construct
SEQUENCE: 140
ttcgcaaagc ctcaaaatcg ggagctcgat gccgagctcg tcgcagag              48

SEQ ID NO: 141        moltype = DNA   length = 48
FEATURE               Location/Qualifiers
source                1..48
                      mol_type = other DNA
                      organism = synthetic construct
SEQUENCE: 141
ttcgcaaagc ctcaaaatcg ggccctcgat gccgagctcg tcgcagag              48

SEQ ID NO: 142        moltype = DNA   length = 48
FEATURE               Location/Qualifiers
source                1..48
                      mol_type = other DNA
                      organism = synthetic construct
SEQUENCE: 142
ttcgcaaagc ctcaaaatcg ggtcctcgat gccgagctcg tcgcagag              48

SEQ ID NO: 143        moltype = DNA   length = 48
FEATURE               Location/Qualifiers
source                1..48
                      mol_type = other DNA
                      organism = synthetic construct
SEQUENCE: 143
ttcgcaaagc ctcaaaatcg ggtgctcgat gccgagctcg tcgcagag              48

SEQ ID NO: 144        moltype = DNA   length = 48
FEATURE               Location/Qualifiers
source                1..48
```

```
                            mol_type = other DNA
                            organism = synthetic construct
SEQUENCE: 144
ttcgcaaagc ctcaaaatcg ggttctcgat gccgagctcg tcgcagag                48

SEQ ID NO: 145              moltype = DNA   length = 50
FEATURE                     Location/Qualifiers
source                      1..50
                            mol_type = other DNA
                            organism = synthetic construct
SEQUENCE: 145
cctttcgggg gatgtgatgt tcgagacgaa gaacatcacc ctgaacatcg              50

SEQ ID NO: 146              moltype = DNA   length = 50
FEATURE                     Location/Qualifiers
source                      1..50
                            mol_type = other DNA
                            organism = synthetic construct
SEQUENCE: 146
cctttcgggg gatgtgatgt tcgagaggaa gaacatcacc ctgaacatcg              50

SEQ ID NO: 147              moltype = DNA   length = 50
FEATURE                     Location/Qualifiers
source                      1..50
                            mol_type = other DNA
                            organism = synthetic construct
SEQUENCE: 147
cctttcgggg gatgtgatgt tcgagccgaa gaacatcacc ctgaacatcg              50

SEQ ID NO: 148              moltype = DNA   length = 50
FEATURE                     Location/Qualifiers
source                      1..50
                            mol_type = other DNA
                            organism = synthetic construct
SEQUENCE: 148
cctttcgggg gatgtgatgt tcgagtcgaa gaacatcacc ctgaacatcg              50

SEQ ID NO: 149              moltype = DNA   length = 50
FEATURE                     Location/Qualifiers
source                      1..50
                            mol_type = other DNA
                            organism = synthetic construct
SEQUENCE: 149
cctttcgggg gatgtgatgt tcgagtggaa gaacatcacc ctgaacatcg              50

SEQ ID NO: 150              moltype = DNA   length = 50
FEATURE                     Location/Qualifiers
source                      1..50
                            mol_type = other DNA
                            organism = synthetic construct
SEQUENCE: 150
cctttcgggg gatgtgatgt tcgagttgaa gaacatcacc ctgaacatcg              50

SEQ ID NO: 151              moltype = DNA   length = 50
FEATURE                     Location/Qualifiers
source                      1..50
                            mol_type = other DNA
                            organism = synthetic construct
SEQUENCE: 151
gtattgggggg aacgcgatat tcgagacgaa gaacatcacc ctgaacatcg             50

SEQ ID NO: 152              moltype = DNA   length = 50
FEATURE                     Location/Qualifiers
source                      1..50
                            mol_type = other DNA
                            organism = synthetic construct
SEQUENCE: 152
gtattgggggg aacgcgatat tcgagaggaa gaacatcacc ctgaacatcg             50

SEQ ID NO: 153              moltype = DNA   length = 50
FEATURE                     Location/Qualifiers
source                      1..50
                            mol_type = other DNA
                            organism = synthetic construct
SEQUENCE: 153
gtattgggggg aacgcgatat tcgagccgaa gaacatcacc ctgaacatcg             50

SEQ ID NO: 154              moltype = DNA   length = 50
FEATURE                     Location/Qualifiers
```

```
source                  1..50
                        mol_type = other DNA
                        organism = synthetic construct
SEQUENCE: 154
gtattgggg aacgcgatat tcgagtcgaa gaacatcacc ctgaacatcg            50

SEQ ID NO: 155          moltype = DNA  length = 50
FEATURE                 Location/Qualifiers
source                  1..50
                        mol_type = other DNA
                        organism = synthetic construct
SEQUENCE: 155
gtattgggg aacgcgatat tcgagtggaa gaacatcacc ctgaacatcg            50

SEQ ID NO: 156          moltype = DNA  length = 50
FEATURE                 Location/Qualifiers
source                  1..50
                        mol_type = other DNA
                        organism = synthetic construct
SEQUENCE: 156
gtattgggg aacgcgatat tcgagttgaa gaacatcacc ctgaacatcg            50
```

MODULAR GENETICALLY ENGINEERED CELL AND METHODS OF GENERATION THEREOF

CROSS-REFERENCE TO RELATED APPLICATIONS

This application claims the benefit of U.S. Provisional Application No. 63/465,759 filed 11 May 2023, which is incorporated in its entirety by this reference.

INCORPORATION BY REFERENCE OF A SEQUENCE LISTING

A Sequence Listing is provided herewith as a Sequence Listing.xml file. The Sequence Listing, created on 1 May 2024, is identified as "SCIX-P03-US.xml" and is 142,694 bytes in size. The content of the Sequence Listing is incorporated in its entirety herein by this reference.

TECHNICAL FIELD

This invention relates generally to the cell engineering field, and more specifically to a new and useful modular genetically engineered cell and methods of generation thereof in the cell engineering field.

DETAILED DESCRIPTION

The following description of the embodiments of the invention is not intended to limit the invention to these embodiments, but rather to enable any person skilled in the art to make and use this invention.

1. Overview

Figure 1:
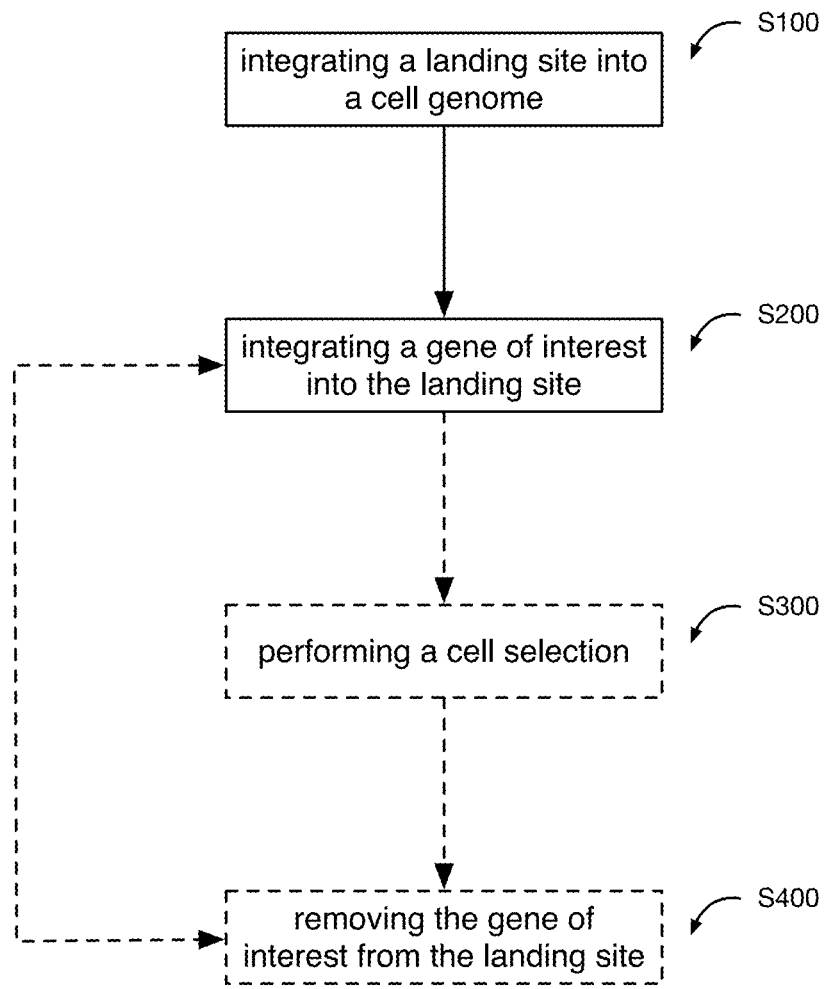
FIG. 1 is a schematic representation of a variant of the method.

As shown in FIG. 1, the method can include: integrating a landing site into a cell genome S100 and integrating a gene of interest into a landing site S200. However, the method can additionally or alternatively include any other suitable steps.

In variants, the method can function to create a cell line that serves as a versatile platform for efficient and targeted integration of multiple transgenes and/or can function to perform a single shot integration of multiple transgenes in a host cell at multiple safe harbor sites. In a specific example, the method can function to create a highly modular cell line that has multiple landing sites in safe harbor sites for further genetic engineering.

2. Examples

In an example, the method includes integrating a landing site at each of a set of target locations (e.g., safe harbor sites) in a genome of a host cell, wherein each landing site includes a pair of site-specific recombinase (SSR) attachment sites. The landing sites can be integrated sequentially or in a single shot. In a specific example, the landing sites each include a unique attachment site pair (e.g., such that one or more SSRs can independently target each landing site for recombination with a corresponding compatible attachment site). A transgene flanked (e.g., bounded) by an attachment site pair compatible with a specific landing site can be integrated into the landing site using an SSR. In an example, a set of transgenes can be integrated into the landing sites (e.g., one transgene integrated into each landing site), wherein the set of transgenes can be integrated sequentially or in a single shot. In a first specific example, the set of transgenes can be integrated in a single shot, using a single vector containing the set of transgenes, each transgene flanked by an attachment site pair. In a second specific example, the set of transgenes can be integrated in a single shot, using multiple (co-transfected) vectors, each vector containing a transgene flanked by an attachment site pair.

The method can optionally include performing a cell selection. In a first example, the method can include: integrating a selectable marker at each of the landing sites using an SSR; performing a cell selection; and excising the selectable markers (e.g., returning each landing site to a pre-recombination state). In a second example, the method can include: integrating a selectable marker simultaneously with integrating a landing site (e.g., integrating the selectable marker flanked by an attachment site pair); performing a cell selection; and excising the selectable marker.

A landing site can optionally include one or more secondary landing sites within the landing site. For example, a landing site can include a secondary pair of attachment sites flanked by a primary pair of attachment sites. In an illustrative example, integrating a landing site can include integrating the following series of sequences: a first attachment site for the primary landing site (e.g., attL1), a first attachment site for the secondary landing site (e.g., attB5), a second attachment site for the secondary landing site (e.g., attB6), an optional gene of interest, and a second attachment site for the primary landing site (e.g., attL2). The primary and secondary landing sites can optionally be integrated in different recombination states (e.g., the primary landing site is attL and the secondary site is attB at initial integration or vice versa, the primary landing site is attR and the secondary site is attP at initial integration or vice versa, etc.).

3. Technical Advantages

Variants of the technology can confer one or more advantages over conventional technologies.

First, integrating multiple transgenes in a cell using conventional strategies (e.g., successively integrating each transgene) can be inefficient, lack target site control, and/or have a limited transgene sequence length. Variants of the technology can create a cell (e.g., a template cell) with multiple landing sites at multiple safe harbor sites, wherein each landing site can efficiently undergo targeted (and directional) transgene integration. This cell can be used to integrate multiple transgenes in a single shot into the cell's multiple landing sites, which can substantially increase efficiency relative to sequentially performing each integration. In a specific example, the multiple transgenes can be integrated using a single vector (e.g., one or more copies of the single vector) containing all of the transgenes, wherein each transgene is bounded by a unique attachment site pair (e.g., a pair of attP sites) that interfaces with a compatible landing site (e.g., a pair of attB sites). This cell can also be used as a template cell, to rapidly experiment with multiple combinations of transgenes. Instead of individually editing, culturing, monitoring, and selecting a previously-unedited host cell for each transgenes combination, experimenters can simply integrate their gene combinations into this pre-edited cell with high confidence of editing success (e.g., reducing the number of repetitions required for culturing, monitoring, and selection steps).

Second, variants of the technology can use prime editing technologies to integrate one or more landing sites into a cell genome, which can increase the efficiency and accuracy of landing site generation. For example, variants of the technology can reduce the sequence length of landing sites to enable successful use of prime editing technologies. In a specific example, attB attachment sites can be used (e.g., instead of attP attachment sites) to reduce the sequence length of the landing sites.

Third, variants of the technology can integrate multiple landing sites (e.g., different landing sites) into a cell genome in a single shot, which can decrease the number of cell selections and increase landing site generation efficiency. For example, using multiple different vectors (each containing one of the landing site sequences to integrate) can be inefficient because only a small proportion of cells would have a successful transfection and integration from each different vector. Variants of the technology can use a single vector containing multiple attachment site pairs (each attachment site pair forming a single landing site) such that a single cell transfection event can generate multiple landing sites in the cell, thus substantially increasing the landing site generation efficiency.

Fourth, variants of the technology can integrate multiple landing sites at a target location, which can increase the number of genes and/or the size of genes that can be integrated at the target location. For example, vectors can have a limited cargo capacity, such that creating a large vector that includes multiple genes of interest (e.g., two genes of interest, greater than two genes of interest, greater than three genes of interest, greater than four genes of interest, etc.) can be extremely challenging or impossible. Variants of the technology can integrate a secondary landing site within a primary landing site (e.g., integrating a sequence that include attachment sites of the primary landing site flanking the secondary landing site). For example, the method can include integrating, into the host cell genome, a landing site that includes a primary pair of attachment sites flanking a first set of genes and a secondary pair of attachment sites. A second set of genes can then be integrated via the secondary pair of attachment sites, resulting in integration of the first set of genes and the second set of genes in the host cell genome. The first set of genes can optionally serve as a backbone for a variety of edits (e.g., a variety of different sets of genes integrated into the second landing site). For example, the second set of genes can be easily exchanged while leaving the first set of genes integrated in the genome.

However, further advantages can be provided by the system and method disclosed herein.

4. Method

As shown in FIG. 1, the method can include: integrating a landing site into a cell genome S100, integrating a gene of interest into a landing site S200, optionally performing a cell selection S300, optionally removing the gene of interest from the landing site S400, and/or any other suitable steps.

All or parts of method can be performed once (e.g., for a single cell), multiple times (e.g., one or more times for each of a set of cells, one or more times for each of a set of landing sites, one or more times for each of a set of genes of interest, etc.), and/or any other number of times. All or portions of the method can be performed iteratively, concurrently, asynchronously, periodically, simultaneously, and/or at any other suitable time.

All or portions of the method can be performed in a single shot (e.g., one shot). For example, single shot integration of a set of sequences (e.g., at least two sequences) into a cell (e.g., host cell) can include performing a single transfection step to integrate the set of sequences. In a first specific example, single shot integration of two sequences into the genome of a cell can include transfection of the cell with one or more copies of a vector that contains both sequences. In a second specific example, single shot integration of two sequences into the genome of a cell can include co-transfection of the cell with: one or more copies of a first vector that contains the first sequence and with one or more copies of a second vector that contains the second sequence.

4.1. Integrating a Landing Site into a Cell Genome S100.

Integrating a landing site into a cell genome S100 functions to create a cell with multiple landing sites at one or more target locations (e.g., safe harbor sites, target genes, etc.). This genetically engineered cell and/or a cell line therefrom can be used as a template or basis for future experimentation (e.g., to rapidly test different transgenes) and/or other future genetic modification (e.g., integrating a target set of transgenes into the cell). S100 is preferably performed for each of a set of landing sites, but can alternatively be performed for a single landing site, performed once for multiple landing sites, and/or otherwise performed. For example, a set of landing sites can be integrated: in a single shot, in multiple shots, iteratively, sequentially, concurrently (e.g., simultaneously), asynchronously, periodically, and/or at any other time.

The cell (e.g., host cell) can be a human cell, any other animal cell, a bacteria cell, and/or any other cell. The cell is preferably a stem cell (e.g., an induced pluripotent stem cell), but can alternatively not be a stem cell. The cell can optionally be a genetically engineered cell. In a specific example, the cell can be a hypoimmunogenic cell (e.g., a hypoimmunogenic stem cell). The cell can be genetically engineered via all or a portion of the method (e.g., wherein the cell is a non-engineered cell prior to all or a portion of the method), genetically engineered prior to all or a portion of the method, a combination thereof, and/or genetically engineered at any other time. The cell can optionally be a part of a cell line, be used to produce a cell line (e.g., the cell is a parent cell for a cell line), and/or otherwise used.

The landing site is preferably one of a set of landing sites, but can alternatively be a singular site. The number of landing sites in the set can be 2-15 or any range or value therebetween (e.g., 2, 3, 4, 5, 6, at least 2, at least 3, at least 4, at least 5, at least 6, a number corresponding to the number of safe harbor sites, a number greater than the number of safe harbor sites, etc.), but can alternatively be 1 or greater than 15. In a first example, each landing site in the set can correspond to a different target location (e.g., genomic locus) in the cell genome. In a second example, two or more landing sites can correspond to the same target location. In a first specific example, two or more landing sites can be arranged sequentially and substantially contiguous (e.g., within 1000 base pairs, within 100 base pairs, within 10 base pairs, within 2 base pairs, etc.) at the target location. In a second specific example, a first landing site can be arranged within a second landing site at the target location.

A landing site can include a pair of attachment sites, wherein the attachment sites can interface with a site-specific recombinase (SSR). The landing site can optionally include one or more additional sequences. The one or more additional sequences can be arranged between the pair of attachment sites (e.g., bounded by the pair of attachment sites, flanked by the pair of attachment sites, etc.), arranged outside the pair of attachment sites (e.g., adjacent to the pair of attachment sites), and/or otherwise arranged. In examples, the additional sequence(s) can include: noncoding DNA, an initial gene (e.g., a selectable marker and/or any other gene of interest), other attachment sites (e.g., for a secondary landing site), a combination thereof, and/or any other sequence. The sequences for the two attachment sites are preferably contiguous (e.g., adjacent), but alternatively an additional sequence can be positioned between the attachment sites.

As used herein, "landing site" can optionally refer to the landing site sequence (e.g., the DNA sequence of the landing site). As used herein, "attachment site" can optionally refer to the attachment site sequence (e.g., the DNA sequence of the attachment site). For example, a landing site sequence can include a pair of attachment site sequences and optionally one or more additional sequences. As used herein, "sequence" preferably refers to a DNA sequence, but can additionally or alternatively refer to an RNA sequence and/or any other genomic sequence.

As used herein, a first sequence and a second sequence bounding (e.g., flanking) a third sequence can refer to an arrangement of sequences where the third sequence is located between the first sequence and the second sequence (e.g., within a vector, within a genome, etc.). In this arrangement, the first sequence and the second sequence are preferably each contiguous with (e.g., adjacent to) the third sequence, but alternatively can be noncontiguous with (e.g., nonadjacent to) the third sequence (e.g., one or more additional sequences can be located between the first sequence and the third sequence and/or between the third sequence and the second sequence).

As used herein, substantially contiguous (e.g., adjacent) sequences can be separated by less than a threshold number of base pairs, wherein the threshold can be between 1 bp-5kbp or any range or value therebetween (e.g., 2 bp, 5 bp, 10 bp, 100 bp, 500 bp, 1kbp, etc.).

Attachment sites can include attB and/or attP sites (e.g., when the landing site is integrated without an initial gene between the attachment sites), attL and/or attR sites (e.g., when the landing site is integrated with an initial gene between the attachment sites), LoxP sites, FRT sites, and/or any other recombination element. The attachment site pair preferably includes non-compatible attachment sites (e.g., the attachment site pair includes two orthogonal attachment sites), but can alternatively include compatible attachment sites (e.g., attB1 and attP1, attB2 and attP2, etc.; attL1 and attR1, attL2 and attR2, etc.). Compatible (e.g., complementary) attachment sites can recombine with one another (e.g., via an SSR, via an SSR and an RDF, etc.) to form hybrid attachment sites; non-compatible (e.g., non-complementary, orthogonal, etc.) attachment sites cannot recombine with one another. In an illustrative example, compatible attachment sites attB1 and attP1 (pre-recombination state) can recombine to form compatible attachment sites attL1 and attR1 (post-recombination state), respectively. In an illustrative example, attB1 is compatible with attP1; attB1 is not compatible with any attB site (e.g., attB1, attB2, attB3, attB4, attB5, attB6, etc.), any attL site, any attR site, attP2, attP3, attP4, attP5, and attP6. The attachment site pair preferably includes only a single type of attachment site (e.g., only attB sites, only attP sites, only attL sites, only attR sites, etc.), but can alternatively include different types of attachment sites (e.g., one attB site and one attP site, one attB site and one attL site, etc.). In an example, all attachment sites across the set of landing sites are not compatible with one another. In another example, no two attachment sites across the set of landing sites are compatible with the same attachment site. Each attachment site in the pair preferably includes a unique attachment site sequence (e.g., a different sequence from the other attachment site), but can alternatively include the same sequence. Each attachment site across all attachment sites in the set of landing sites preferably includes a unique attachment site sequence (e.g., a different sequence from every other attachment site in the set of landing sites), but can alternatively include the same sequence as other attachment sites. In a specific example, there are no repeats within the cell genome across attB1, attB2, attB3, attB4, attB5, attB6, attL1, attL2, attL3, attL4, attL5, and attL6. In a first example, the attachment site pair can include any two different attB sequences selected from: attB1 (TT mutant), attB2 (AG mutant), attB3 (AC mutant), attB4 (TG mutant), attB5 (CC mutant), and attB6 (TC mutant). In a second example, the attachment site pair can include any two different attL sequences selected from: attL1 (TT mutant), attL2 (AG mutant), attL3 (AC mutant), attL4 (TG mutant), attL5 (CC mutant), and attL6 (TC mutant).

The attachment sites in the attachment site pair are preferably inverted relative to one another (e.g., the attachment site pair is an inverted attachment site pair), but can alternatively not be inverted. An inverted attachment site pair in a sequence (e.g., genome, vector, etc.) can be a pair of attachment sites with opposite orientations in the sequence. The orientation of an attachment site can be defined relative to the interface between the attachment site and a unidirectional SSR; the unidirectional SSR would interface with each attachment site in an inverted attachment site pair in opposite directions. Additionally or alternatively, the orientation of an attachment site in an attachment site pair can be defined by a shared sequence between the two attachment sites in the pair; when the shared sequences are oriented in opposite directions, the attachment site are inverted relative to one another. For example, a landing site sequence can include a pair of attachment site sequences inverted relative to each other.

Attachment site sequences (e.g., used in S100, S200, and/or any other part of the method) can include any of SEQ ID NOS: 1-156. In some cases, an attachment site sequence includes a nucleotide sequence that differs by 1, 2, 3, 4, or 5 nucleotides from any of SEQ ID NOs:1-156.

The size of an attachment site and/or the size of the landing site (e.g., including or not including homology arms used in integration) can optionally be less than a threshold number of base pairs. The threshold can be between 40 bp-1 kb or any range or value therebetween (e.g., 40 bp, 70 bp, 80 bp, 90 bp, 100 bp, 150 bp, etc.), but can alternatively be less than 40 bp or greater than 1 kb.

The target location of the landing site is preferably a (pre-existing) genomic safe harbor site, but can alternatively not be a safe harbor site (e.g., when the landing site is used to alter function of the cell) and/or can be any other site (e.g., locus) in the cell genome. In a first specific example, the target location can be a noncoding region of the genome. In a second specific example, the target location can be a location within a gene (e.g., an exon of the gene, a coding region of the gene, etc.), wherein integrating the landing site sequence can knock out the gene and/or otherwise alter function of the gene. In examples: one landing site can be located at a single target location (e.g., safe harbor site); one landing site can be located at each of a set of target locations; multiple landing sites (e.g., arranged sequentially and substantially contiguous; one landing site arranged within another landing site; etc.) can be located at a single target location; multiple landing sites can be located at each of a set of target locations (e.g., a different landing site for each target location, multiple landing sites for one or more target locations, etc.); a combination thereof; and/or any other mapping between landing site(s) and target location(s) can be used. When multiple landing sites are incorporated into the same cell, the landing sites are preferably different (e.g., heterogeneous; include different attachment site combinations, different attachment site order, include unique attachment site sequences; etc.); alternatively, different safe harbor sites can have the same landing sites. Specific examples of safe harbor sites include: AAVS1 locus (an intronic region of the PPP1R12C gene), hROSA26 locus (an intronic region of the THUMPD3 gene), CCR5 locus, H11 locus (an intergenic region on chromosome 22), CLYBL locus, and/or any other safe harbor loci.

When multiple target locations are used (e.g., with one or more landing sites at each target location), the target locations are preferably noncontiguous (e.g., non-adjacent), but can additionally or alternatively be contiguous (e.g., adjacent). In an example, the target locations can be different safe harbor sites. In a specific example, the method can include integrating a first landing site sequence into a first site (e.g., first target location) in a genome of a cell, the first landing site sequence including a first pair of attachment site sequences; and integrating a second landing site sequence into a second site (e.g., second target location) in the genome of the cell, the second site noncontiguous with the first site, the second landing site sequence including a second pair of attachment site sequences. The number of base pairs separating target locations can optionally be greater than a threshold; the threshold can be 1 bp-1 million bp or any range or value therebetween (e.g., greater than 5 bp, greater than 10 bp, greater than 100 bp, greater than 1kbp, greater than 10kbp, greater than 100kbp, etc.), but can alternatively be less than 1 bp or greater than 1 million bp. Target locations can optionally be located on different chromosomes.

Figure 3:
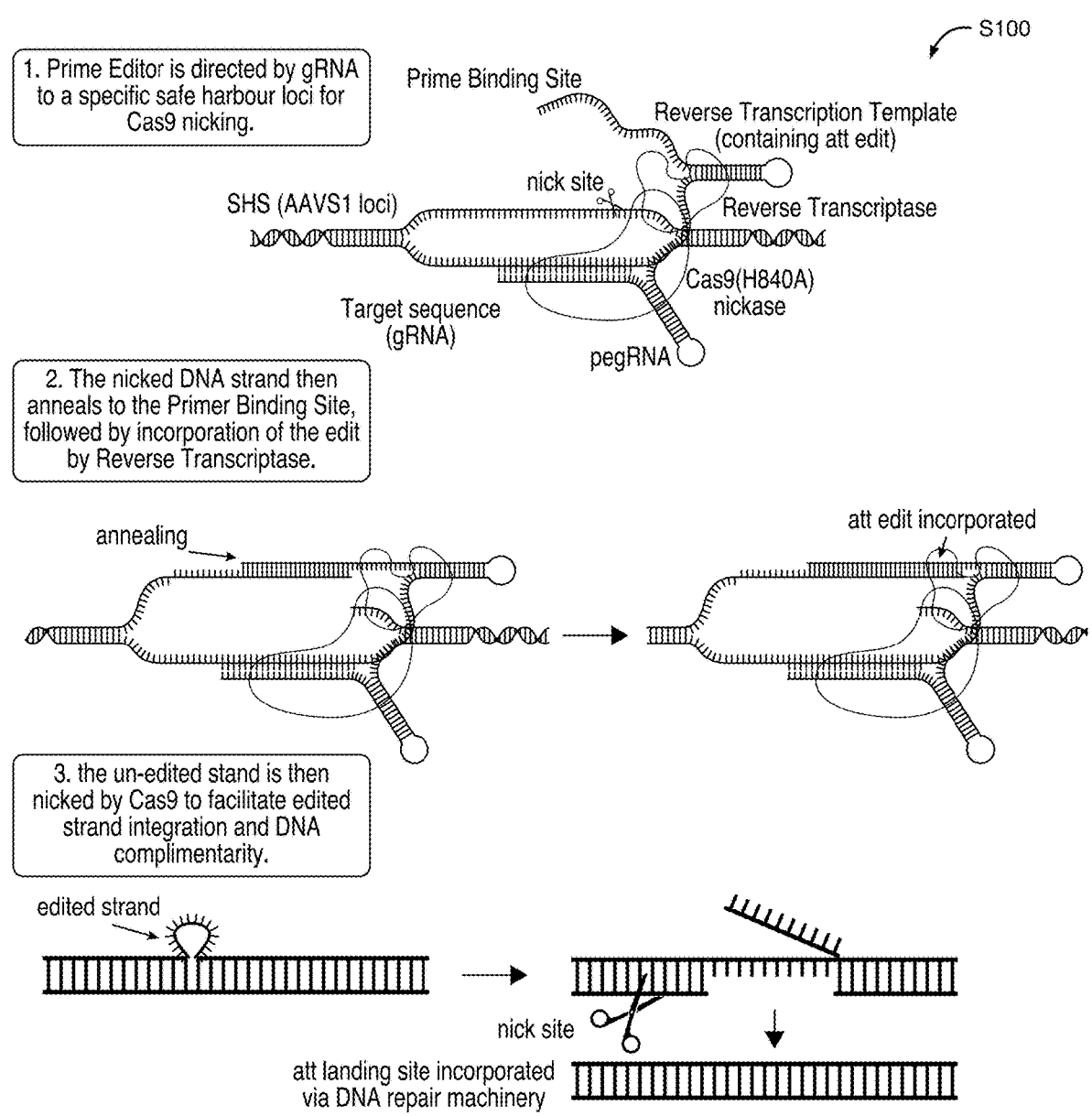
FIG. 3 depicts an illustrative example of integrating a landing site into a host cell genome using prime editing.

The landing site can be integrated at the target location using prime editing (e.g., example shown in FIG. 3), homology-directed repair (HDR) (e.g., homologous recombination), any other CRISPR technology, and/or any other integration (e.g., knock-in) method. In a specific example, the landing site can be integrated at the target location using CRISPR/Cas9-mediated HDR. In a specific example, vector (s) used for landing site integration can include Cas9 and/or reverse transcriptase. In a first example, the landing site can be integrated using a single shot method (e.g., single shot prime editing, single shot HDR, etc.). In a second example, the landing site can be integrated using a multi-shot method.

Figure 2A:
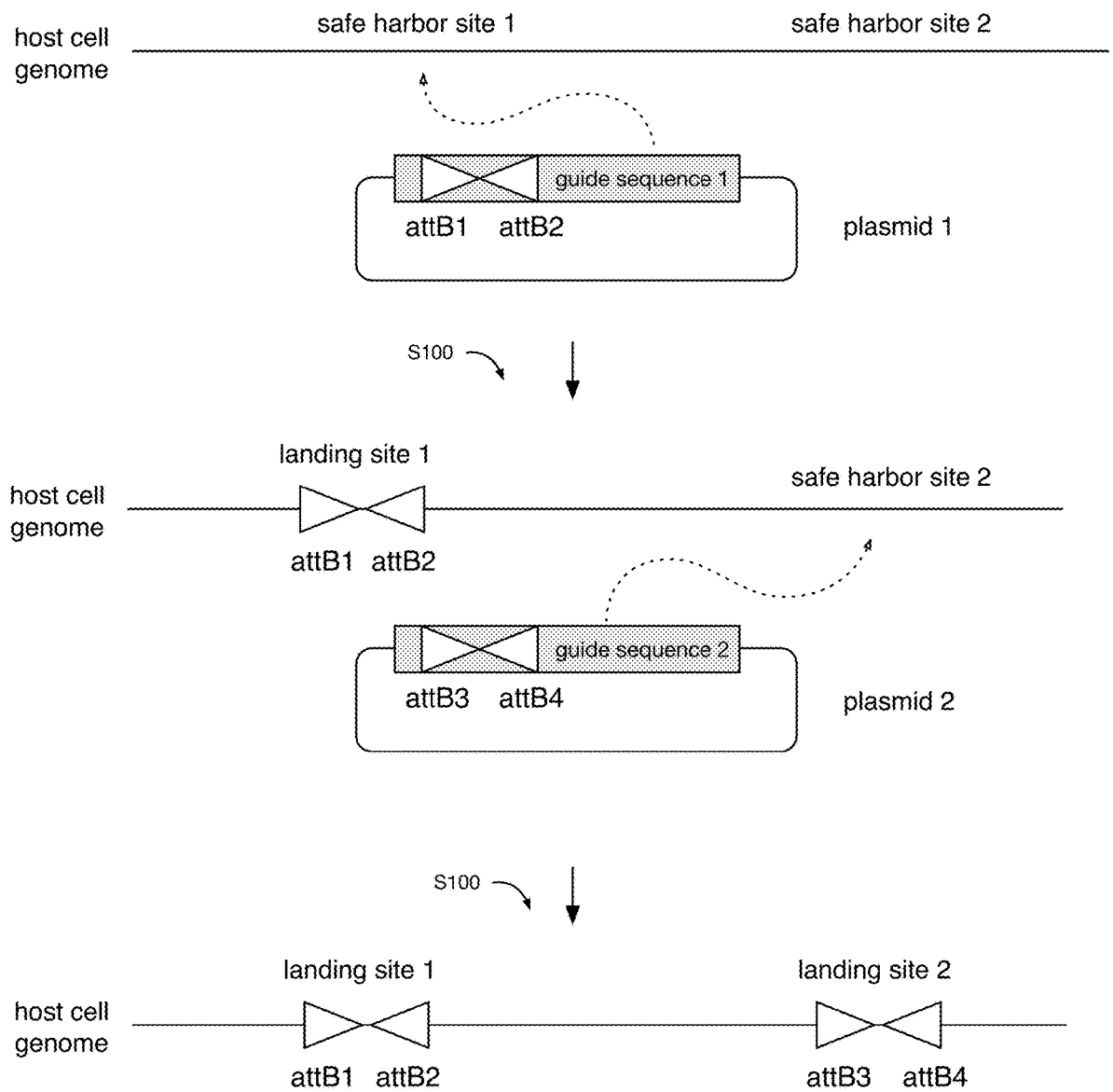
FIG. 2A depicts an example of integrating landing sites into a host cell genome in two shots.
Figure 2B:
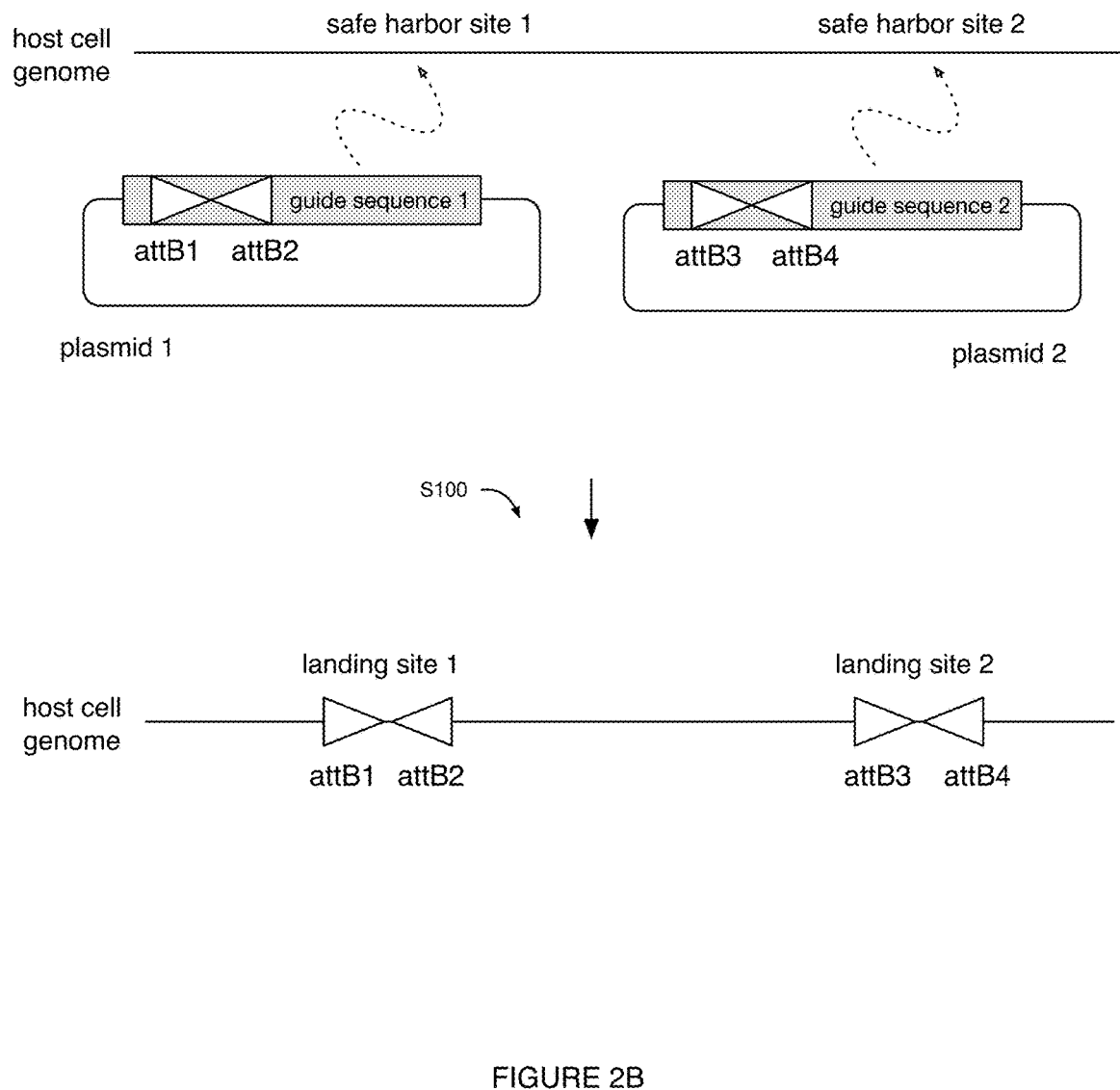
FIG. 2B depicts an example of integrating landing sites into a host cell genome in a single shot, using multiple (co-transfected) vectors.
Figure 2C:
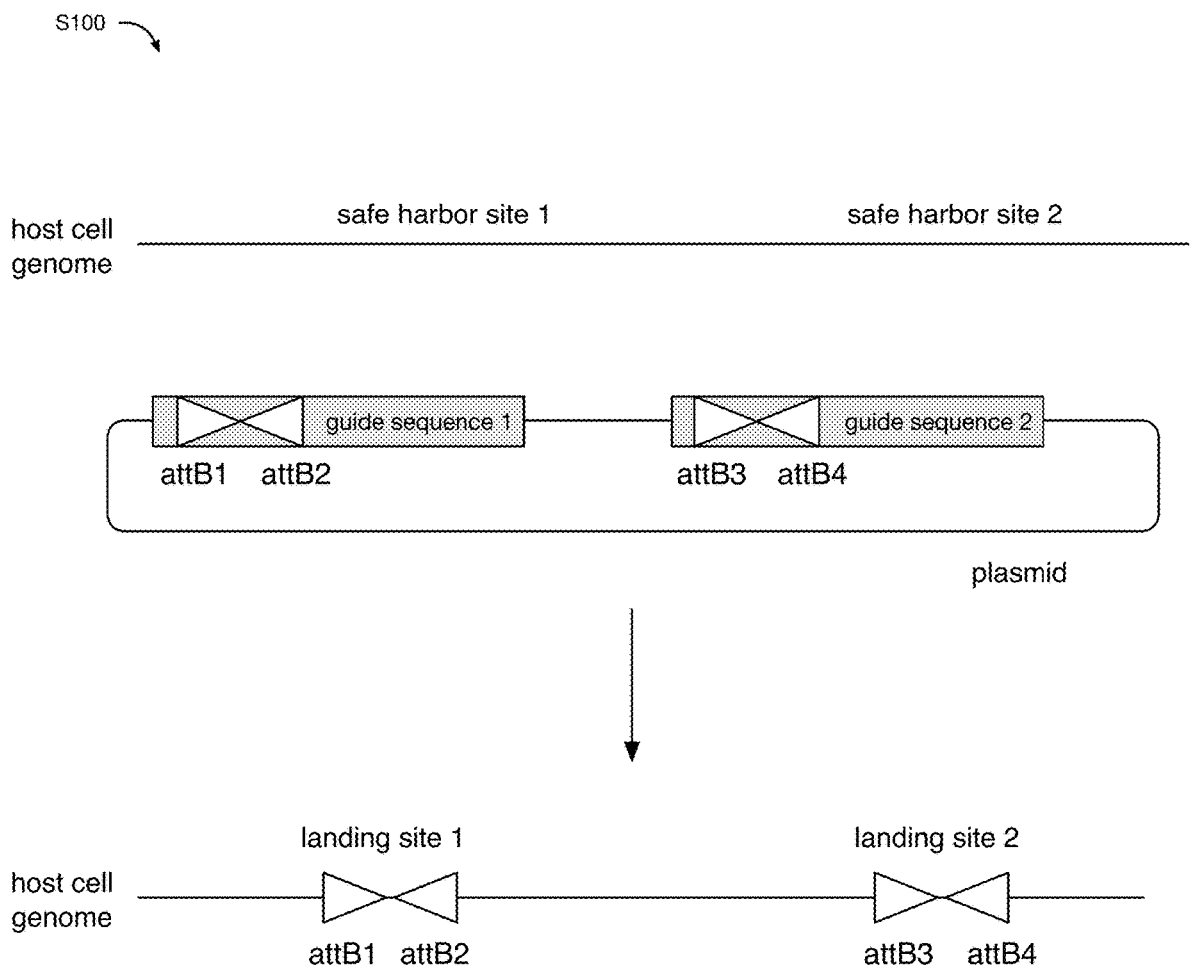
FIG. 2C depicts an example of integrating landing sites into a host cell genome in a single shot, using a single vector.
Figure 2D:
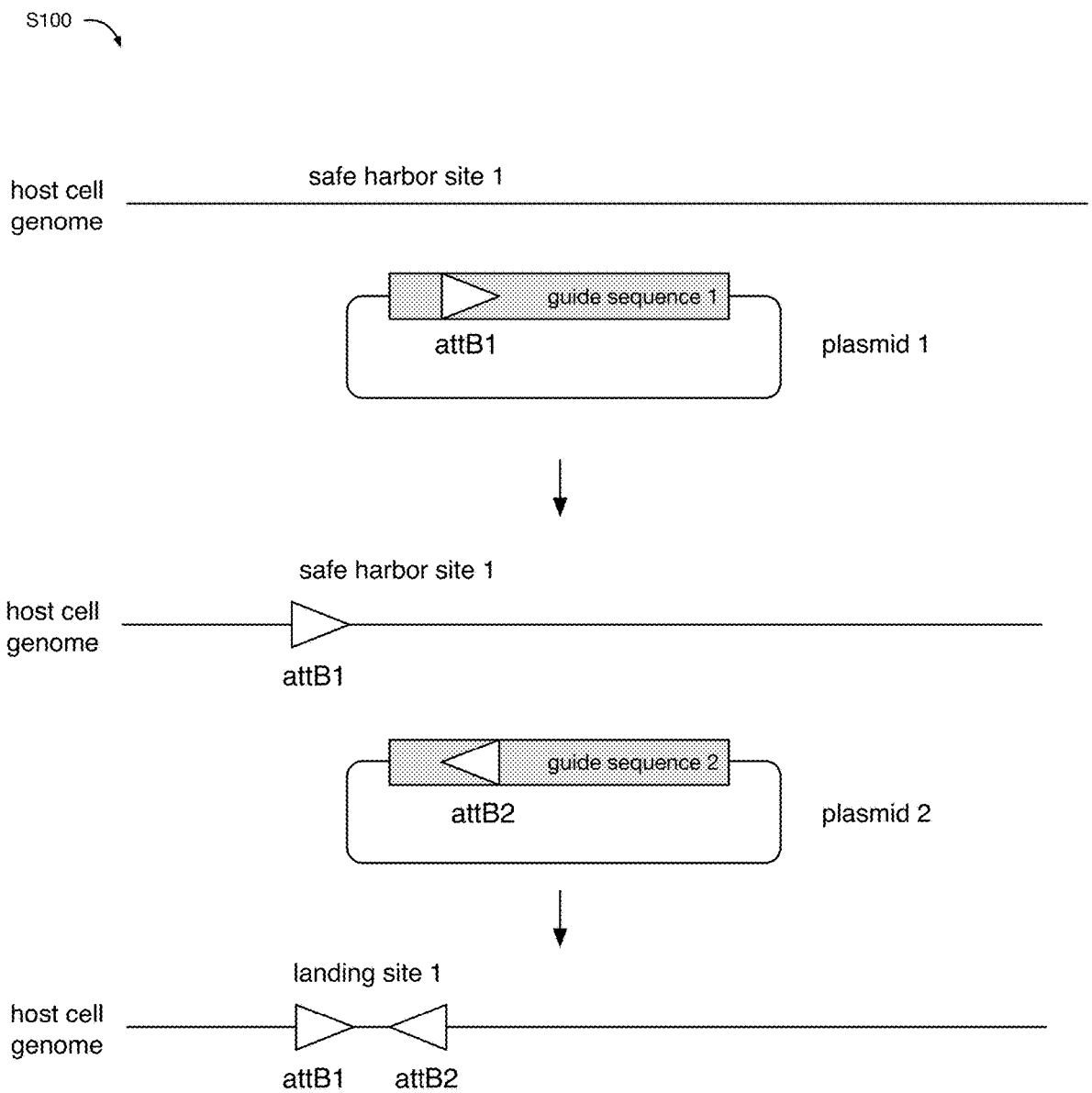
FIG. 2D depicts an example of integrating a landing site into a host cell genome by separately integrating each attachment site.
Figure 2E:
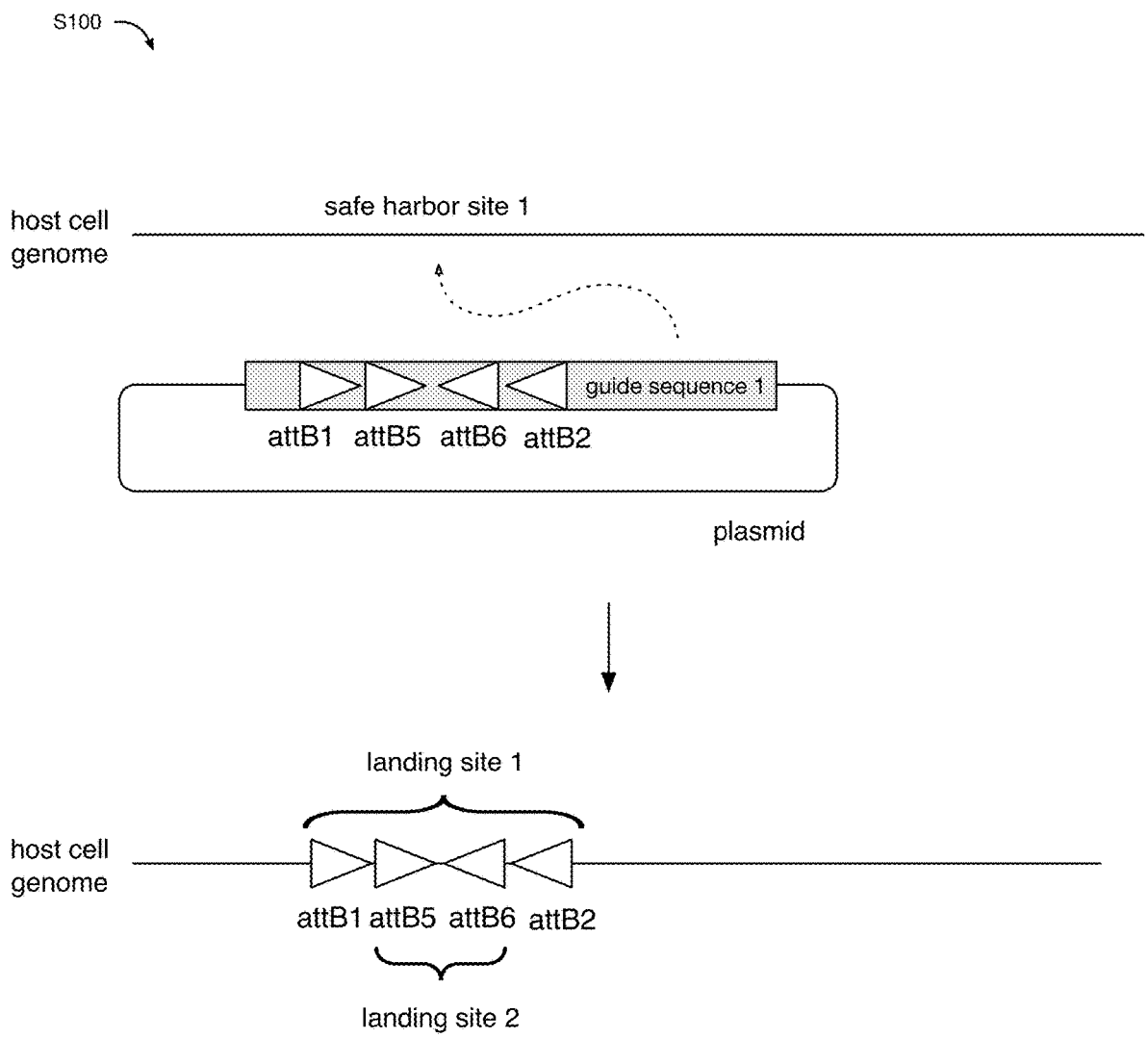
FIG. 2E depicts an example of integrating multiple landing sites, including a secondary landing site within a primary landing site, into a host cell genome.
Figure 2F:
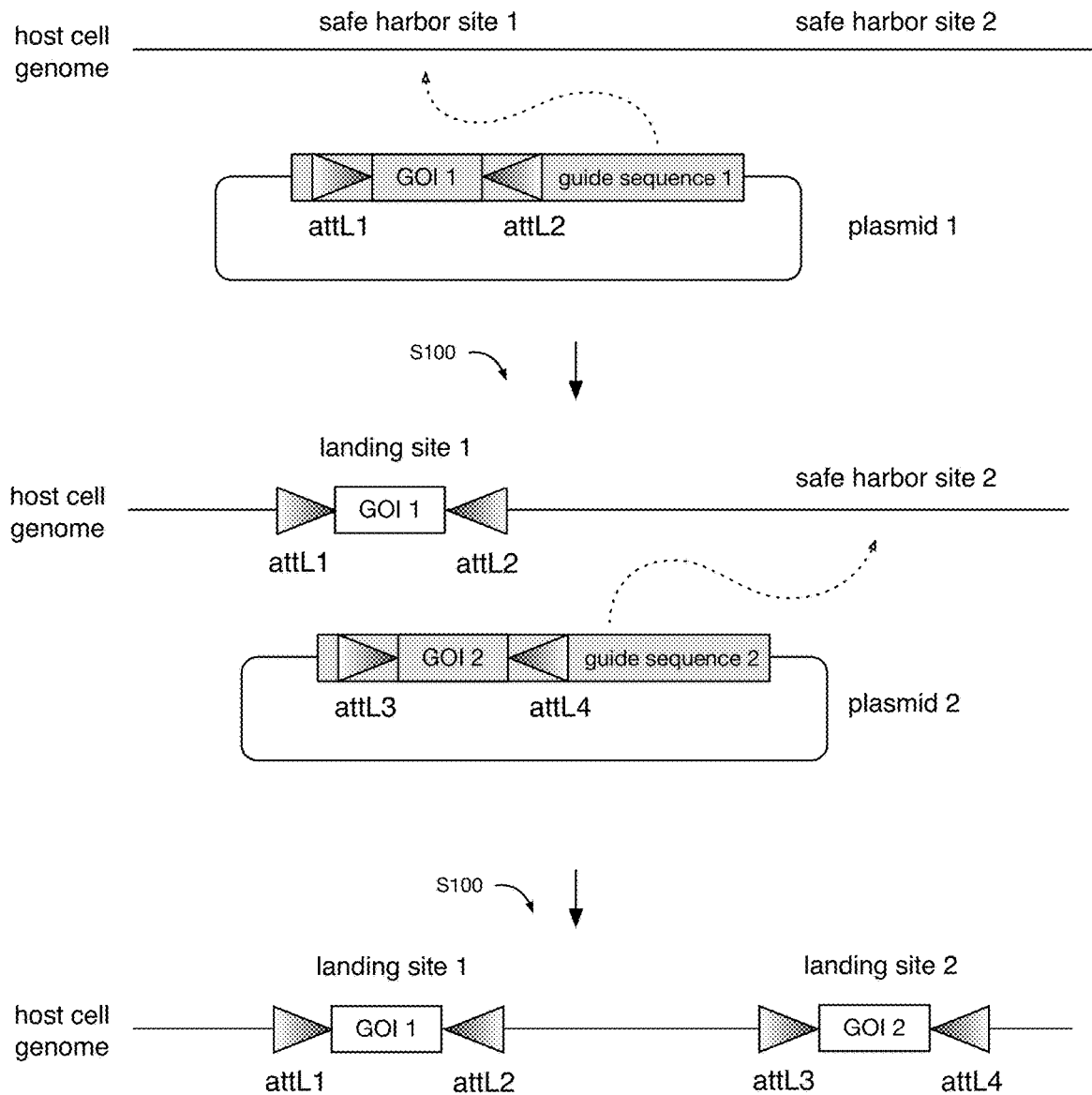
FIG. 2F depicts an example of integrating landing sites into a host cell genome in two shots, wherein each landing site includes attachment sites bounding (e.g., flanking) a gene of interest.
Figure 2G:
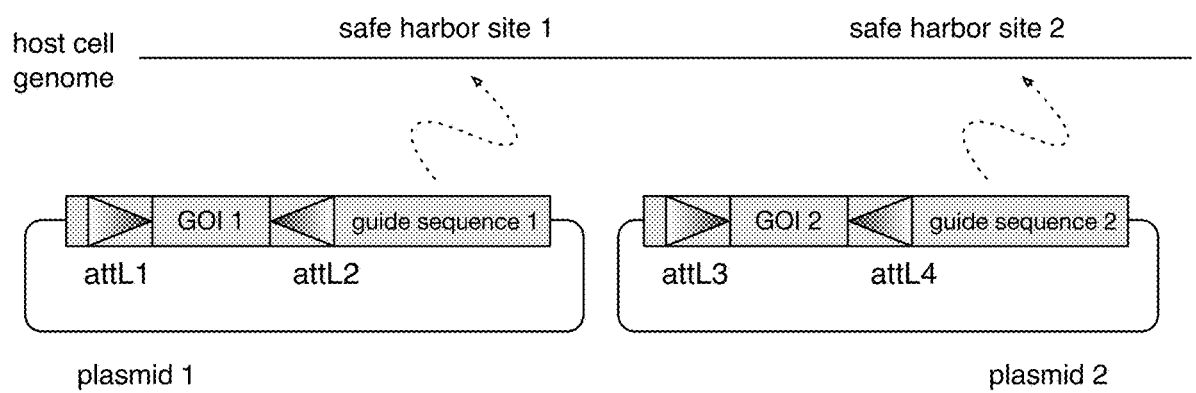
FIG. 2G depicts an example of integrating landing sites into a host cell genome in single shot, using multiple (co-transfected) vectors, wherein each landing site includes attachment sites bounding a gene of interest.
Figure 2G:
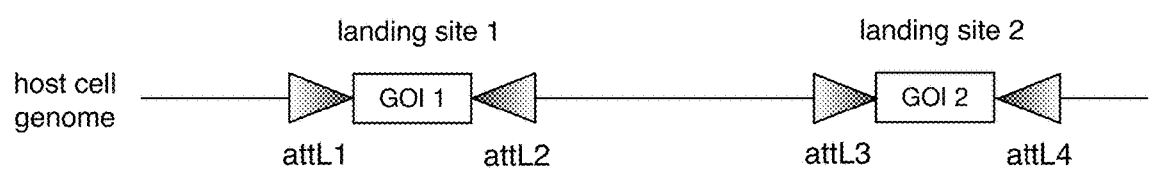

In a first variant, integrating the landing site includes transfecting the cell (e.g., host cell) with one or more vectors (e.g., plasmids, constructs, etc.), wherein each vector contains a single landing site. For example, the vector can contain: one pair of attachment sites within one guide sequence, wherein the guide sequence maps the attachment site pair to the corresponding landing site target location. In a first example, multiple vectors transfect the cell in sequence (e.g., in multiple shots); examples are shown in FIG. 2A and FIG. 2F. In a second example, multiple vectors co-transfect the cell (e.g., in a single shot); examples are shown in FIG. 2B and FIG. 2G.

Figure 2H:
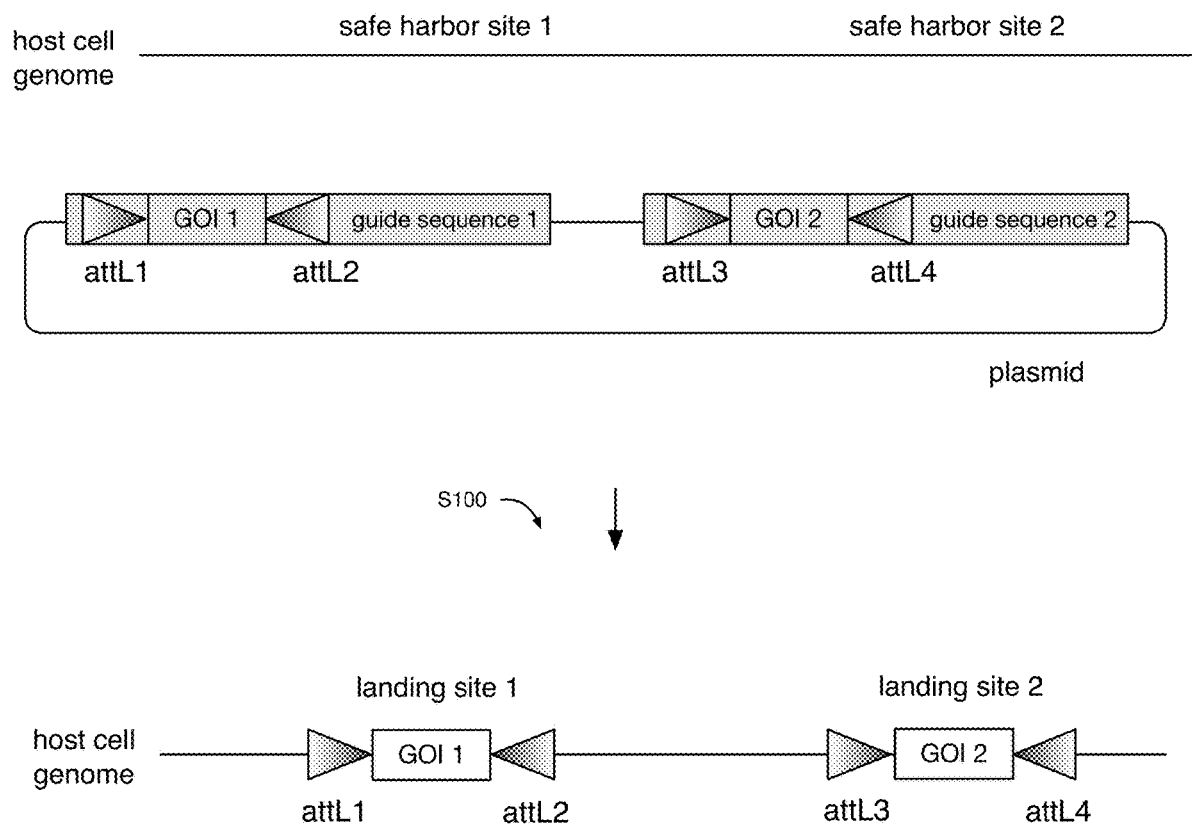
FIG. 2H depicts an example of integrating landing sites into a host cell genome in single shot, using a single vector, wherein each landing site includes attachment sites bounding a gene of interest.
Figure 2I:
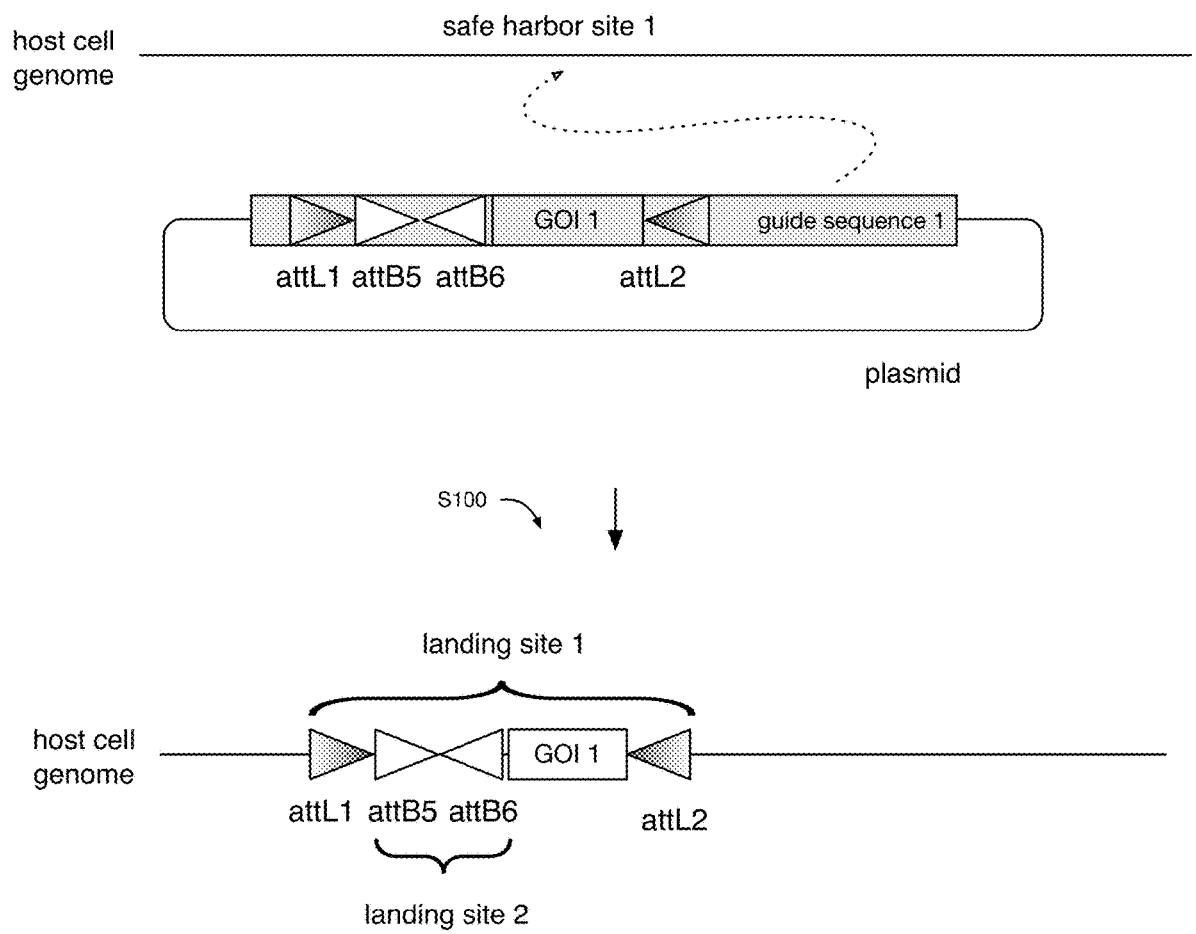
FIG. 2I depicts an example of integrating multiple landing sites, including a secondary landing site within a primary landing site, into a host cell genome, wherein the primary landing site includes attachment sites bounding the secondary landing site and a gene of interest.

In a second variant, integrating the landing site includes transfecting the cell (e.g., host cell) with one or more vectors, wherein each vector contains multiple landing sites. In a first example, multiple landing sites are integrated at multiple locations in a single shot. Examples are shown in FIG. 2C and FIG. 2H. For example, the vector can contain: multiple pairs of attachment sites, each within a corresponding guide sequence to map the attachment site pair to its corresponding landing site target location. In a specific example, a first landing site sequence and a second landing site sequence are integrated in a single shot by transfecting the cell with a vector containing the first landing site sequence and the second landing site sequence. In a second example, multiple landing sites are integrated (simultaneously) at a single location in a single shot. Examples are shown in FIG. 2E and FIG. 2I. For example, the vector can contain: one or more secondary pairs of attachment sites (corresponding to secondary landing sites) arranged within a primary pair of attachment sites (corresponding to a primary landing site), the attachment sites within a corresponding guide sequence to map the set of landing sites to its corresponding landing site target location. In a specific example, a primary landing site sequence can include a primary pair of (inverted) attachment site sequences and a secondary landing site sequence bounded by the primary pair of attachment site sequences, the secondary landing site including a secondary pair of (inverted) attachment site sequences. In an illustrative example, the primary pair of attachment site sequences can include attachment site sequence in a first state (e.g., post-recombination state; hybrid state; etc.), and the secondary pair of attachment site sequences can attachment site sequences in a second state (e.g., pre-recombination state; non-hybrid state; etc.). For example, the primary pair of attachment site sequences can be one of a pair of attL sequences or a pair of attR sequences and the secondary pair of attachment site sequences can be one of a pair of attB sequences or a pair of attP sequences. The primary landing site can optionally include one or more genes of interest, wherein the gene(s) of interest can be arranged within the secondary landing site (e.g., bounded by the secondary attachment site sequences), within the primary landing site (e.g., bounded by the secondary landing site and one of the primary attachment site sequences), outside the primary attachment site sequences, a combination thereof, and/or otherwise arranged.

In a third variant, integrating the landing site includes transfecting the cell (e.g., host cell) with one or more vectors, wherein each vector contains a single attachment site of the landing site. An example is shown in FIG. 2D. For example, a first vector contains a first attachment site (from the attachment site pair) within a first guide sequence to map the first attachment site to a first target location corresponding to the landing site; a second vector contains a second attachment site (from the same attachment site pair) within a second guide sequence to map the second attachment site to a second target location corresponding to the same landing site.

However, one or more landing sites can be otherwise generated.

4.2. Integrating a Gene of Interest into a Landing Site S200.

Integrating a gene of interest (GOI) into a landing site S200 functions to integrate one or more transgenes into the cell genome at one or more landing sites. For example, the genetically engineered cell and/or a cell line therefrom (e.g., the cell is a parent cell of the cell line) can undergo efficient and targeted integration and/or replacement of transgenes at the landing sites. In a specific example, S200 can function to perform recombination-mediated cassette exchange at the landing site(s). S200 can be performed after S100, concurrent with S100 (e.g., where the landing site sequence integrated in S100 includes the gene of interest), after S300, after S400, and/or at any other time. S200 can be performed once, one or more times for each of a set of landing sites, one or more times of each of a set of GOIs, one or more times for each of a set of cells, and/or any other number of times.

Multiple GOIs can optionally be integrated into landing sites in the cell genome (e.g., one GOI for each of a set of landing sites, multiple GOIs in a single landing site, a combination thereof, etc.). In a first variant, the GOIs are integrated into the landing sites sequentially. In a first example, a first GOI (e.g., a selectable marker) is integrated into a landing site (e.g., a first iteration of S200, concurrently with S100 wherein the landing site includes the first GOI, etc.); the GOI is removed from the landing site (e.g., S400); and a second GOI is integrated into the same landing site (e.g., a second iteration of S200). In a second example, a first GOI is integrated into a first landing site in the cell (e.g., a first iteration of S200, concurrently with an instance of S100 wherein the first landing site includes the first GOI, etc.); and a second GOI is integrated into a different landing site in the same cell (e.g., a second iteration of S200, concurrently with an instance of S100 wherein the second landing site includes the second GOI, etc.). In a third example, a combination of the first and second examples can be used. In a second variant, the GOIs are integrated into the landing sites in a single shot. For example, a first GOI can be integrated into a first landing site (e.g., a first instance of S200, concurrently with an instance of S100 wherein the landing site includes the first GOI, etc.) and a second GOI can be integrated into a second landing site in the cell (e.g., a second instance of S200, concurrently with an instance of S100 wherein the second landing site includes the second GOI, etc.) using a single transfection step (e.g., using one or more copies of a single plasmid, using co-transfection of multiple plasmids, etc.). In a specific example, the method can include integrating, in a single shot: a first gene of interest into a first landing site sequence; and a second gene of interest into a second landing site sequence. In a specific example, integrating a first gene of interest and a second gene of interest in a single shot can include: transfecting the cell with a vector containing the first gene of interest and the second gene of interest.

A GOI can include one or more genes. Examples of a GOI and/or genes therein can include: a selectable marker (e.g., selection marker), kill switch gene (e.g., suicide gene), transcription factor, opsin, cell differentiation genes, cell adhesion molecule genes, hypoimmunogenicity genes, fluorophore genes, cell surface molecule expression genes, one or more attachment sites, a landing site, any transgene, multiple genes (in sequence), and/or any other DNA sequence. In a specific example, the GOI can include a (secondary) landing site (e.g., a pair of attachment sites), wherein S200 includes integrating the (secondary) landing site into a (primary) landing site. Examples of selectable markers include: genes that confer antibody resistance (e.g., puromycin N-acetyl-transferase, aminoglycoside kinase, hygromycin B phosphotransferase, Sh ble, etc.), genes that confer fluorescence (e.g., GFP, eGFP, RFP, BFP, mCherry, etc.), and/or any other gene that can be used for cell selection. The size of the GOI can optionally be greater than a threshold number of base pairs; the threshold can be between 0bp-1 kb or any range or value therebetween (e.g., 100 bp, etc.), but can alternatively be greater than 1 kb. The size of the GOI can optionally be less than a threshold number of base pairs; the threshold can be between 5 kb-100 kb or any range or value therebetween (e.g., 10 kb, etc.), but can alternatively be less than 5 kb or greater than 100 kb.

Integrating a GOI can include integrating a cassette into a landing site, wherein the cassette can be or include the GOI. For example, integrating a GOI can include: creating a vector (e.g., plasmid) containing the cassette bounded by a pair of attachment sites, transfecting the cell (e.g., host cell) with the vector, and integrating the cassette into a landing site using an SSR and optionally a phage-encoded recombination directionality factor (RDF). In a first specific example, RDF is not used when the landing site includes attB or attP sites and the cassette is bounded by (compatible) attL or attR sites. In a second specific example, RDF can be used when the landing site includes attL or attR sites and the cassette is bounded by (compatible) attB or attP sites. The pair of attachment sites bounding (e.g., flanking) the cassette in the vector is preferably compatible with the target landing site's attachment site pair, and preferably interfaces with the same SSR as the corresponding landing site attachment site pair. However, the GOI attachment sites can be otherwise configured. The vector can optionally include multiple cassettes, each cassette bounded by a pair of attachment sites compatible with a landing site. For example, a single vector can be used to integrate multiple GOIs at different landing sites.

The pair of attachment sites bounding the cassette can include attB sites, attP sites, attL sites, attR sites, LoxP sites, FRT sites, and/or any other recombination element. The attachment site pair bounding the cassette preferably includes only a single type of attachment site (e.g., only attB sites, only attP sites, etc.), but can alternatively include different types of attachment sites (e.g., one attB site and one attP site). The attachment sites in the attachment site pair are preferably orthogonal; but can alternatively not be orthogonal. The attachment sites in the attachment site pair are preferably inverted relative to one another, but can alternatively not be inverted.

The pair of attachment sites bounding the cassette preferably map to the pair of attachment sites in the landing site (e.g., the attachment site pair bounding the GOI are compatible with the landing site attachment site pair). For example, a first attachment site in the vector maps to a first attachment site in the landing site, and a second attachment site in the vector maps to a second attachment site in the landing site. In a specific example, each attachment site in the vector uniquely maps to an attachment site in the one or more landing sites. In a first illustrative example, the landing site includes attB1 and attB2 attachment sites, and the vector contains the GOI bounded by attP1 (mapping to attB1) and attP2 (mapping to attB2) attachment sites. In a second illustrative example, the landing site includes attL1 and attL2 attachment sites, and the vector contains the GOI bounded by attR1 (mapping to attL1) and attR2 (mapping to attL2) attachment sites. Examples of vectors are shown in FIG. 6, FIG. 7, FIG. 8, and FIG. 9.

Figure 4A:
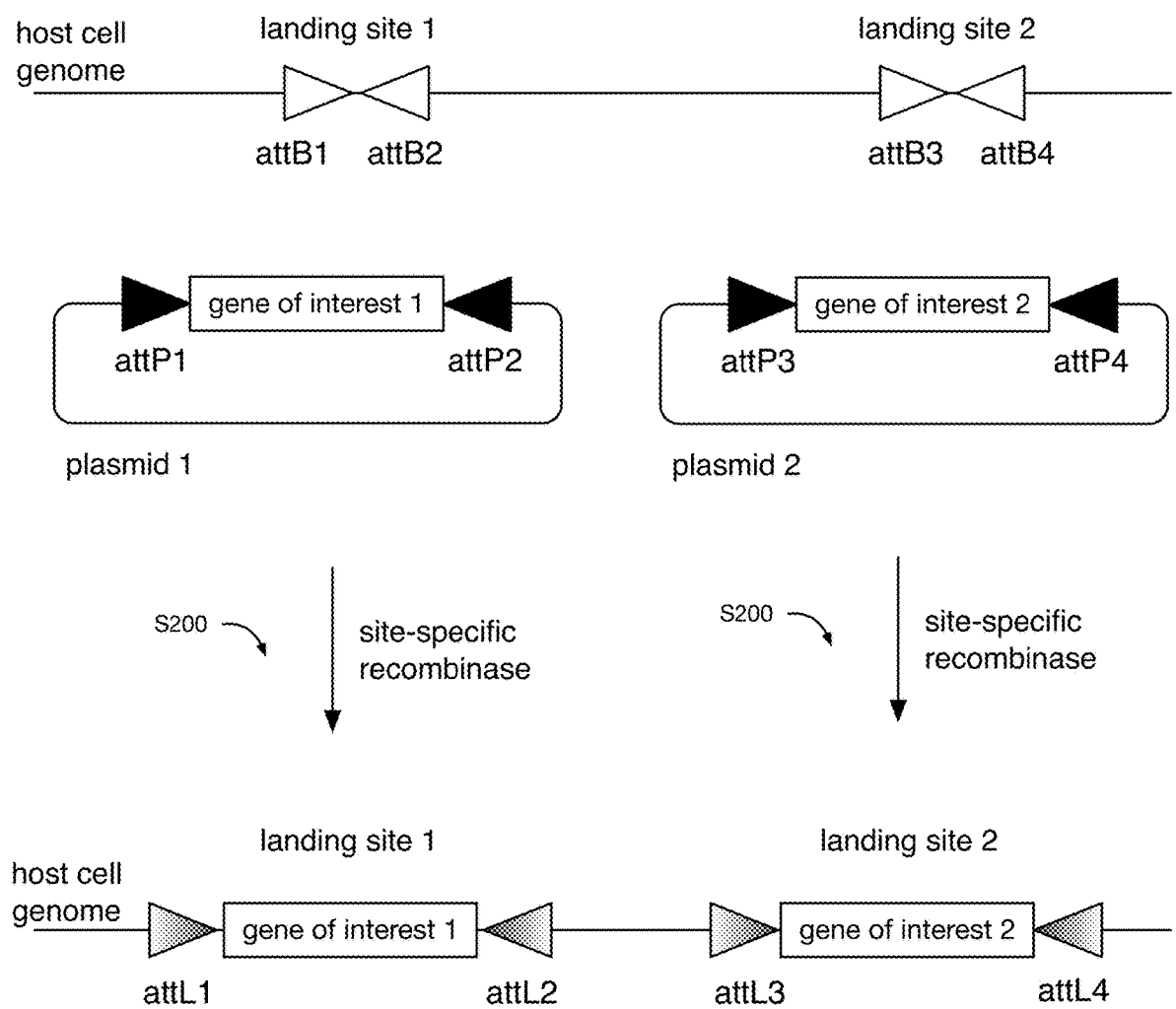
FIGS. 4A-4C depict examples of integrating one or more genes of interest into a set of landing sites.

In a first variant, each vector contains a single GOI. An example is shown in FIG. 4A. For example, the vector can contain: a pair of attachment sites bounding a GOI. In an example, multiple (different) vectors are used, each vector containing a GOI, wherein each GOI is integrated into a corresponding landing site based on the attachment site pair bounding the GOI (e.g., example shown in FIG. 5). The cell can be transfected with one or more copies of each different vector. In a first example, the multiple vectors transfect the cell in sequence (e.g., in multiple shots). In a second example, the multiple vectors co-transfect the cell (e.g., in a single shot).

Figure 4B:
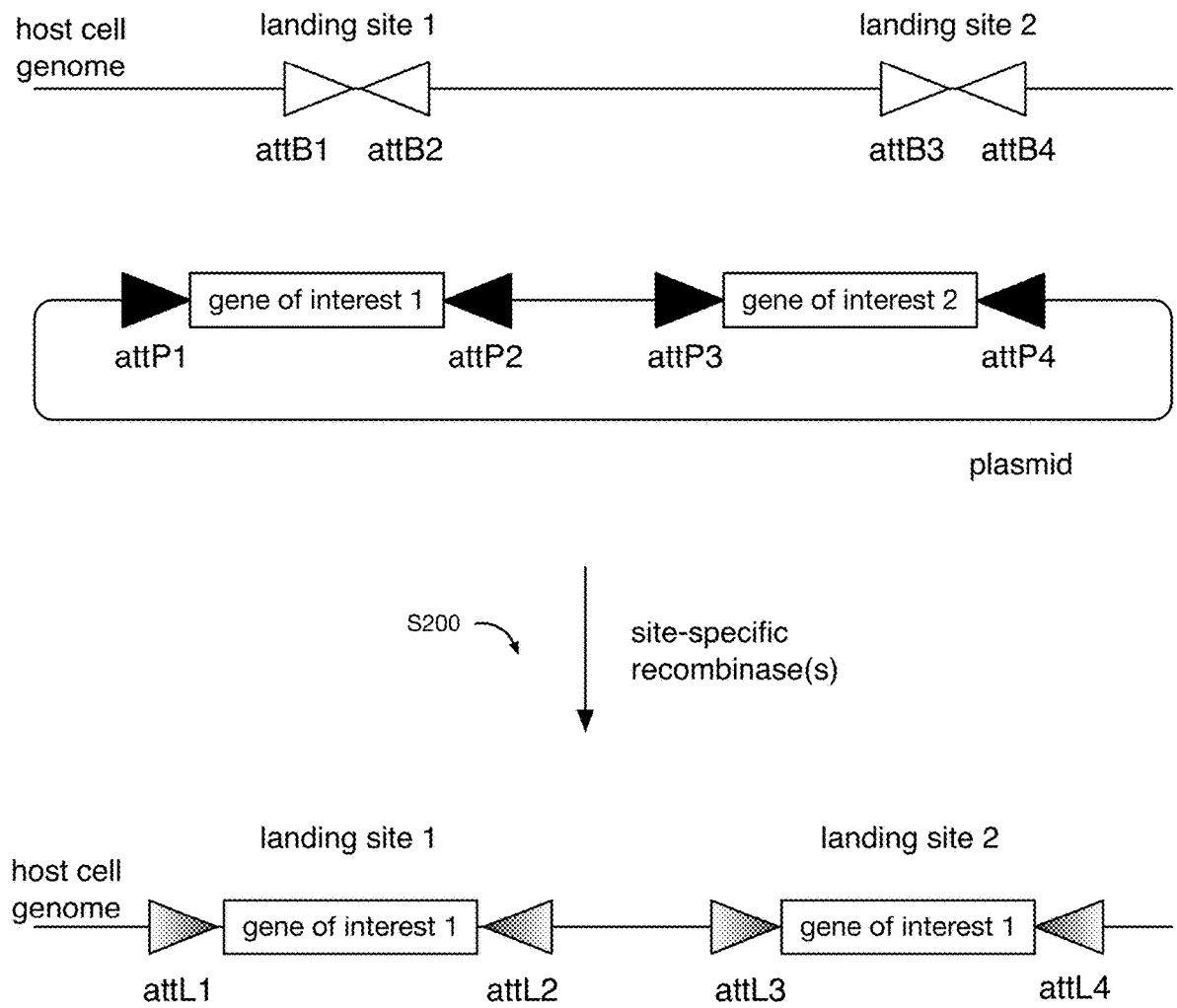

In a second variant, a single vector can contain multiple GOIs. An example is shown in FIG. 4B. For example, the vector can contain: multiple pairs of attachment sites, each bounding a corresponding GOI, wherein each GOI in the vector is mapped to a landing site based on the corresponding attachment site pair. The single vector (e.g., a single copy of the single vector, multiple copies of the single vector, etc.) can be used to integrate the multiple GOIs into multiple landing sites (e.g., performing multiple instances of S200 in a single shot). In a first illustrative example, a first copy of the vector (containing the set of GOIs) integrates a first GOI in the set of GOIs into a first landing site, and a second copy of the vector (containing the set of GOIs) integrates a second GOI in the set of GOIs into a second landing site. In a second illustrative example, the single vector can sequentially integrate each GOI in a set of GOIs into each corresponding landing site (e.g., the single vector becomes shorter after each integration, replacing the GOI and bounding attachment sites in the vector with a pair of hybrid attachment sites).

Figure 4C:
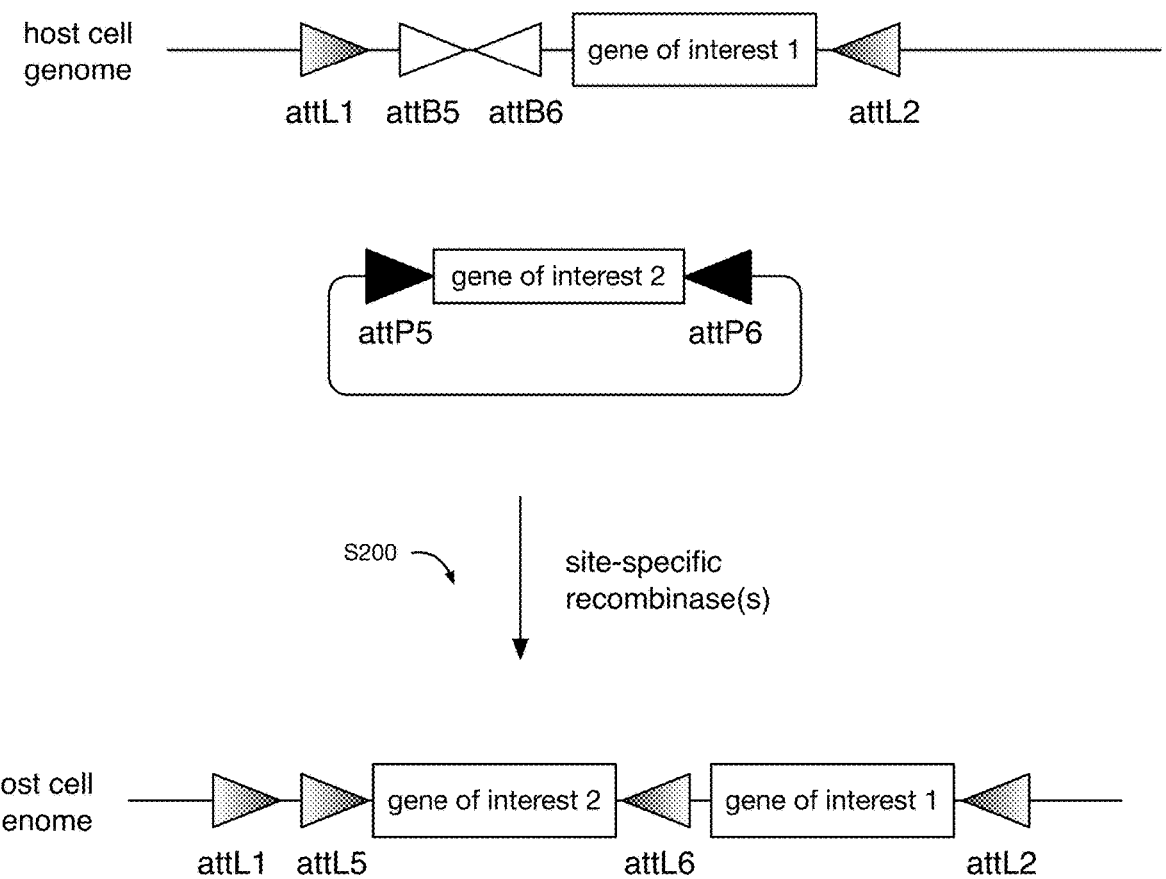

The GOI can optionally be integrated into a secondary landing site (e.g., a landing site within a primary landing site). An example is shown in FIG. 4C. In an illustrative example, the primary landing site (after S100) includes a pair of attachment sites (e.g., attL sites) bounding: a pair of attB sites (the secondary landing site) and optionally one or more additional sequences (e.g., an initial GOI adjacent to the secondary landing site, within the primary landing site). In this illustrative example, S200 can include integrating the GOI into the secondary landing site, transforming the pair of attB sites into a pair of attL sites. In a specific example, the GOI can include a (tertiary) landing site, such that, after the GOI is integrated into a secondary landing site in the cell genome, the genome includes: a primary landing site, a secondary landing site within the primary landing site, and a tertiary landing site within the secondary landing site.

Figure 5:
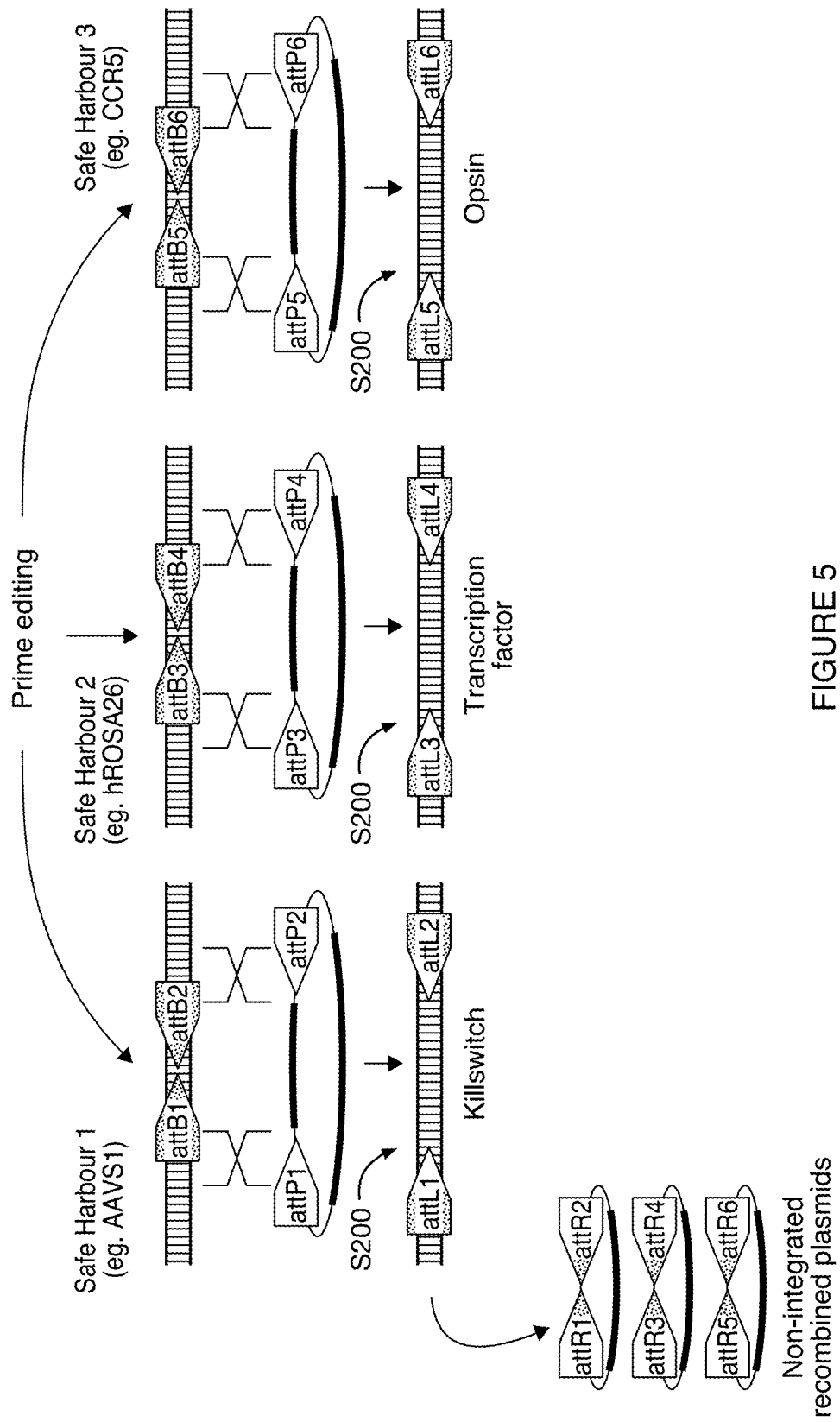
FIG. 5 depicts an illustrative example of integrating a set of genes of interest into a set of landing sites.
Figure 6:
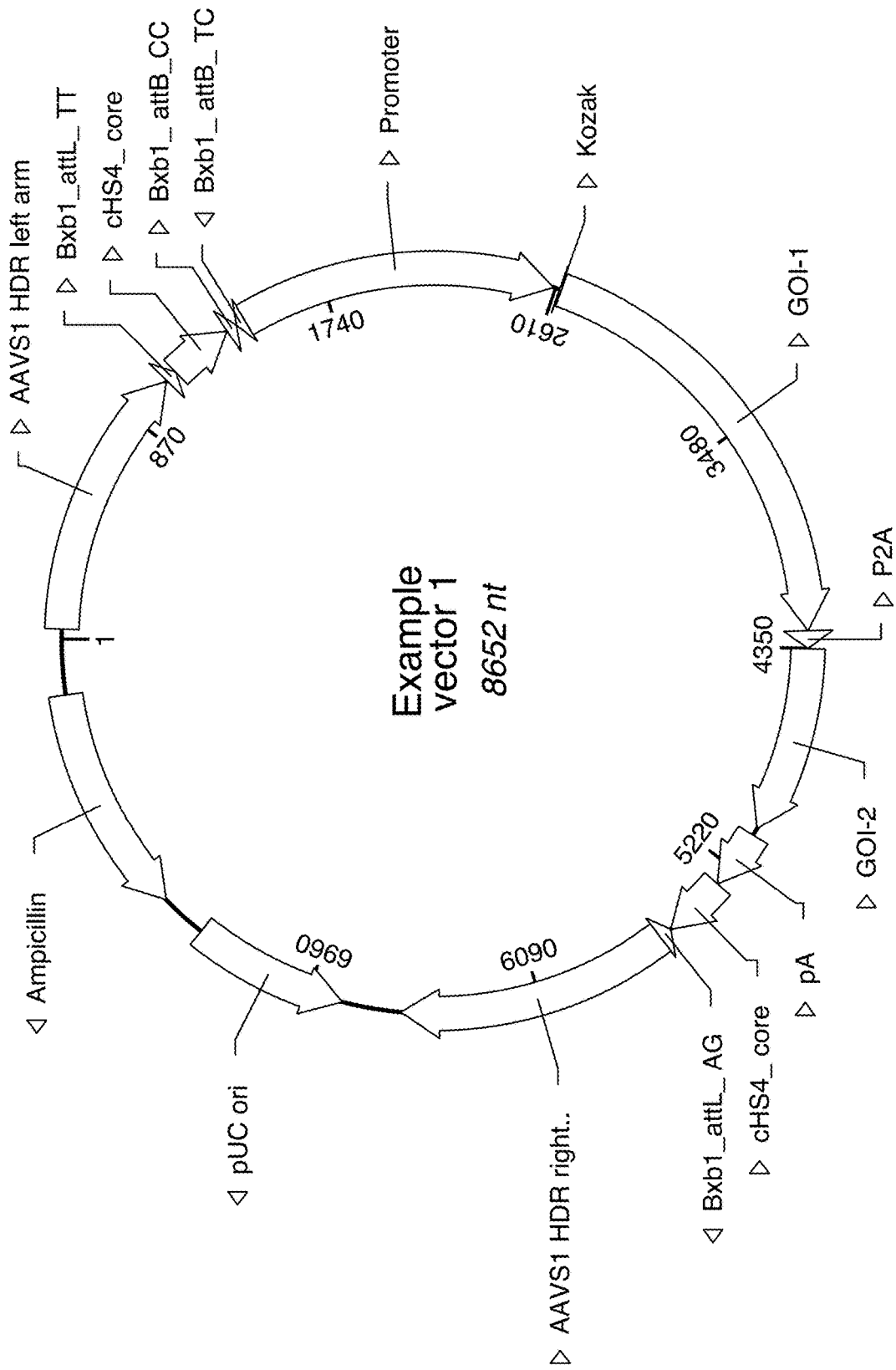
FIG. 6 depicts an illustrative example of a vector carrying a landing site (including attachment sites: attL_TT and attL_AG) that includes a secondary landing site (including attachment sites: attB_CC and attB_TC) and set of genes of interest (GOI-1 and GOI-2).
Figure 7:
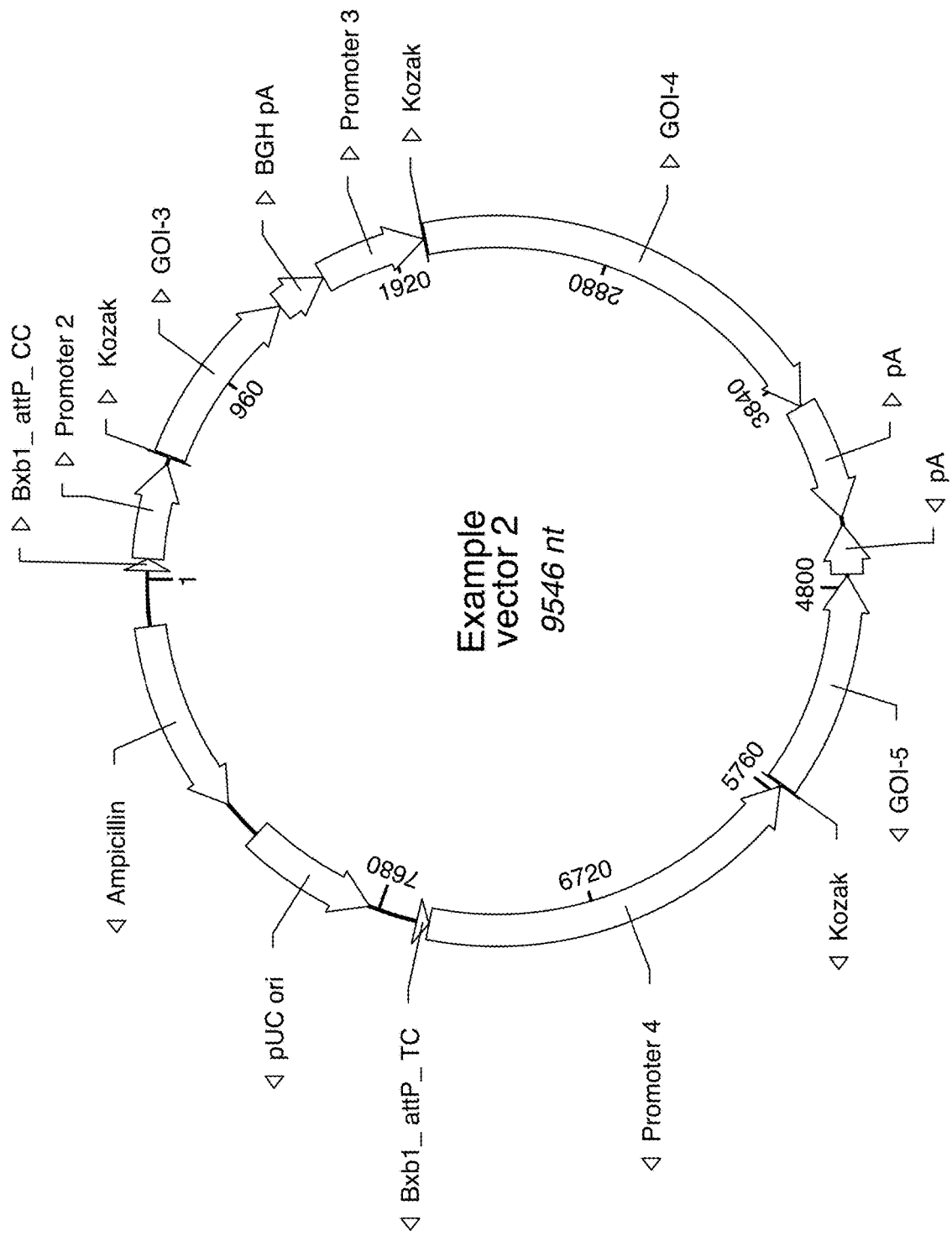
FIG. 7 depicts another illustrative example of a vector carrying a set of genes of interest (GOI-3, GOI-4, and GOI-5) bounded by an attachment site pair (attP_CC and attP_TC) that can interface with a landing site (e.g., via a site-specific recombinase). In a specific example, the attachment site pair can interface with the secondary landing site of FIG. 6.
Figure 8:
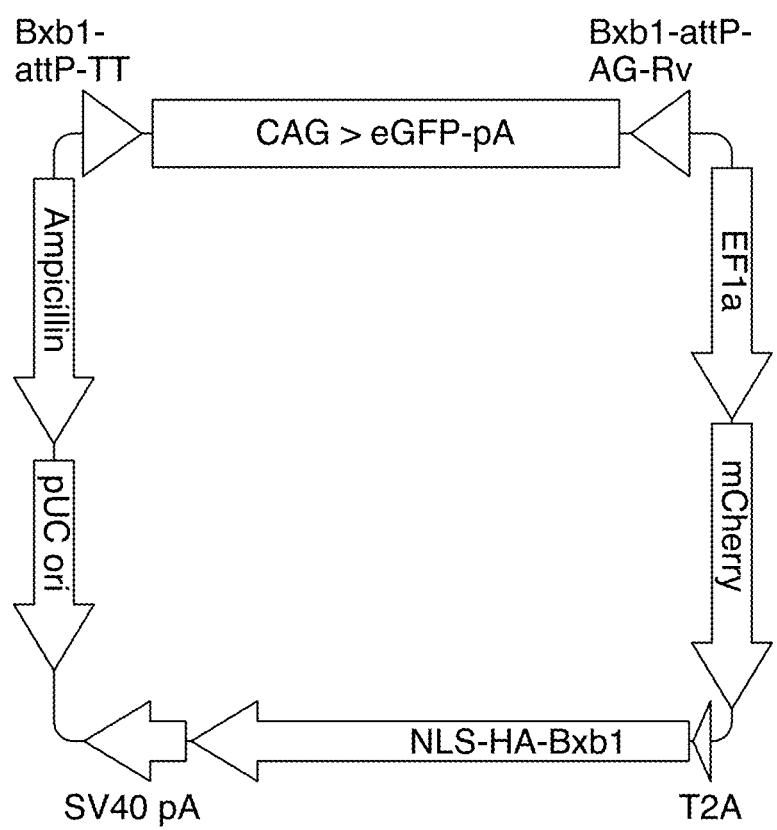
FIG. 8 depicts a first illustrative example of a vector carrying a gene of interest (e.g., wherein the gene of interest includes: CAG>eGFP-pA).
Figure 9:
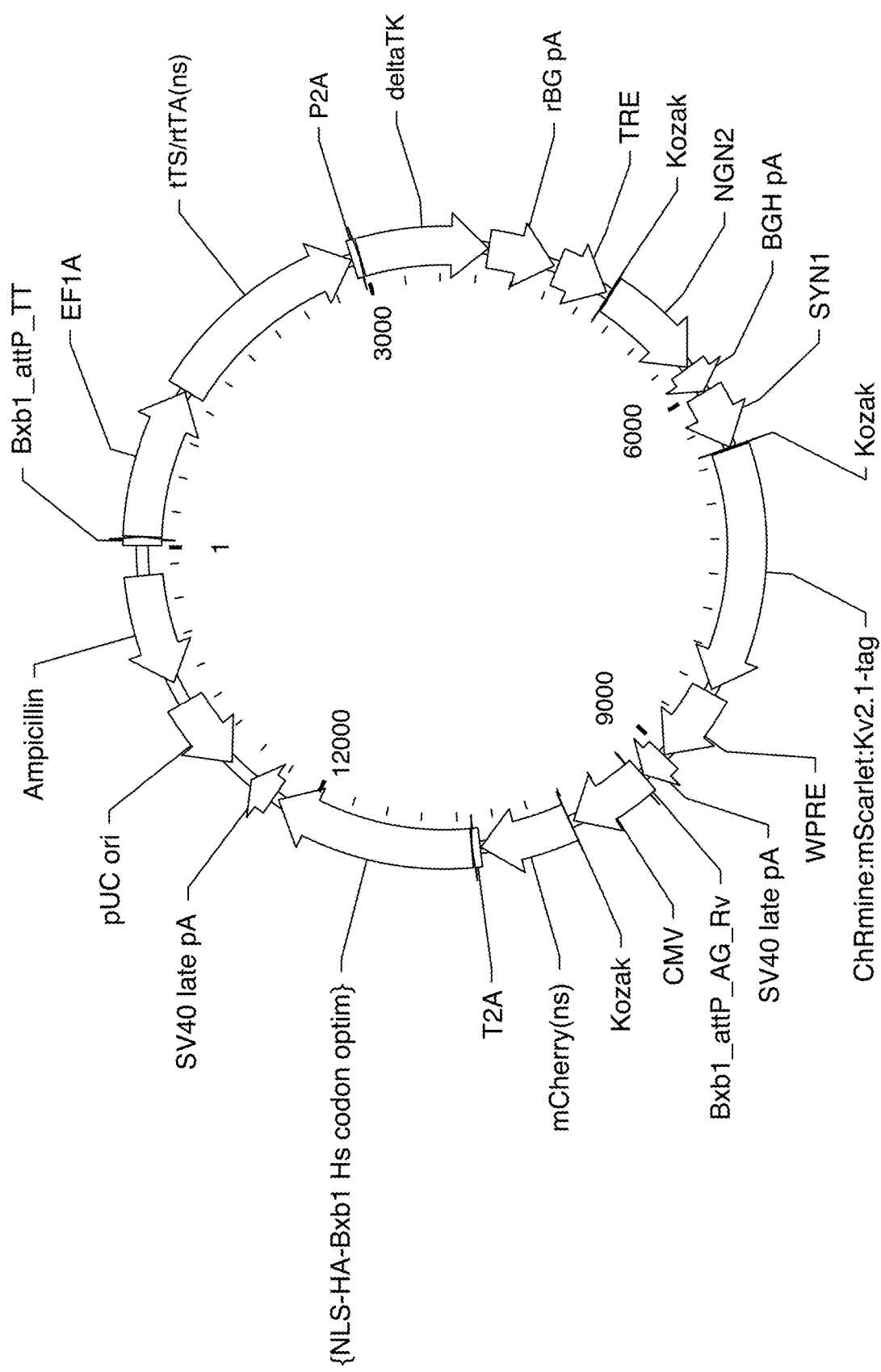
FIG. 9 depicts a second illustrative example of a vector carrying a gene of interest (e.g., wherein the gene of interest includes: transcription factor rtTA, killswitch deltaTK, inducible NGN2 gene, and optogenetic actuator ChRmine).

The GOI is preferably integrated into the landing site using an SSR; an example is shown in FIG. 5. However, the GOI can alternatively be integrated into the landing site using any other enzyme or combination of enzymes. The SSR (e.g., a serine integrase, a tyrosine integrase, etc.) is preferably a unidirectional SSR, but can alternatively not be unidirectional. Examples of SSRs include: phiC31, Bxb1, Peaches, Benedict, Veracruz, Rebeuca, Theia, Cre, FLP, and/or any other integrase or other SSR. Integrating the GOI into the landing site using an SSR can include transforming the attachment sites in the landing site into hybrid sites (e.g., attB and/or attP attachment sites can be transformed to attL and/or attR hybrid sites), and optionally generating residual vectors (e.g., non-integrated recombined vectors). Multiple GOIs can be integrated using the same SSR and/or different SSRs.

However, the GOI can be otherwise integrated into the landing site.

4.3. Performing a Cell Selection S300.

The method can optionally include performing a cell selection S300, which functions to select one or more cells with one or more landing sites properly integrated into the genome. S300 can be performed after S100 (e.g., wherein a landing site is integrated into the genome with an initial selectable marker gene) to create the template cell, but can additionally or alternatively be performed after S200 (wherein the GOI includes a selectable marker), and/or at any other time.

Performing a cell selection can include identifying one or more cells from a set of cells that includes one or more selectable markers, wherein the presence of a selectable marker can indicate presence of a corresponding landing site in the cell genome.

Figure 11A:
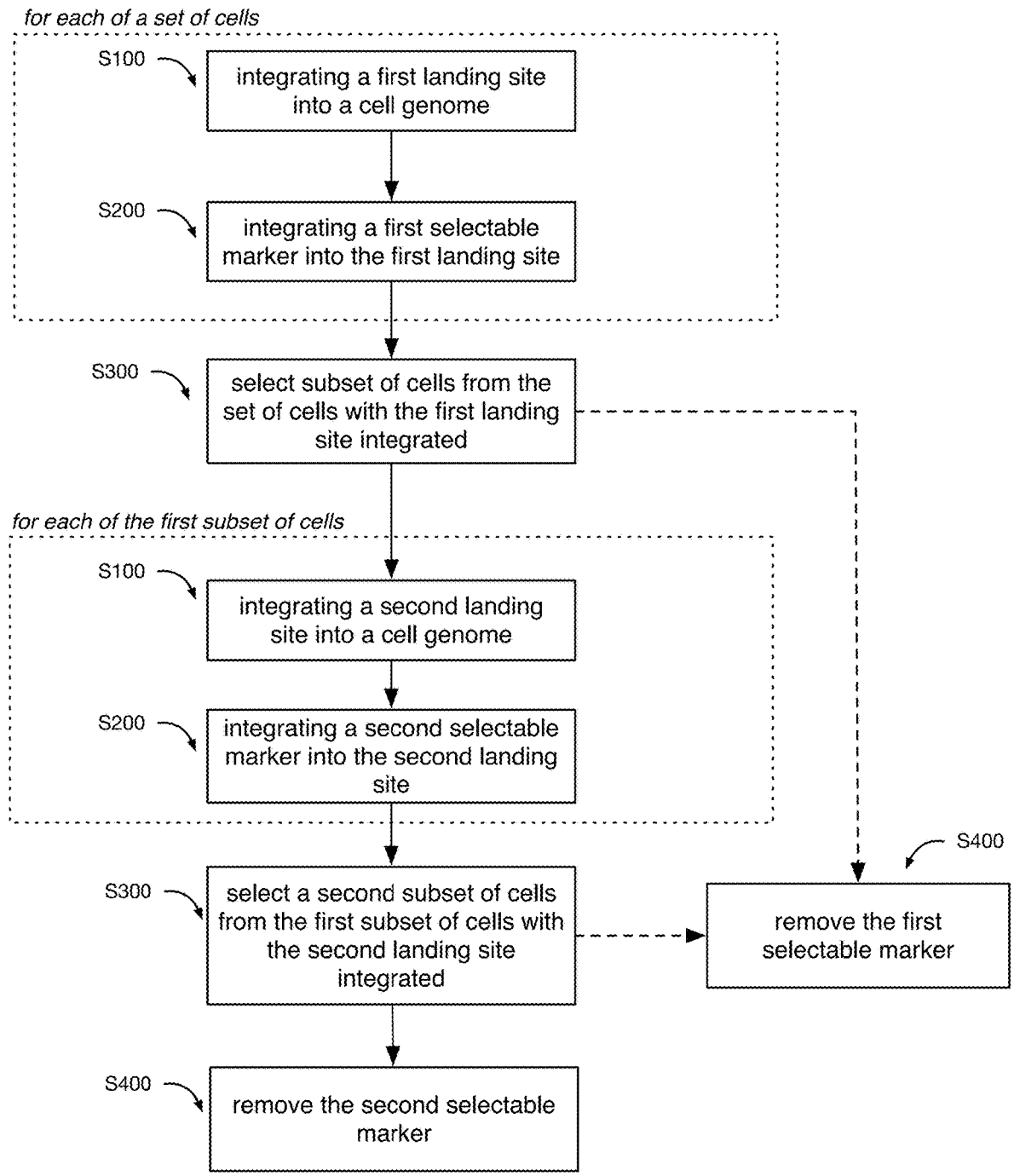
FIGS. 11A and 11B depict schematic representations of examples of performing cell selections.

In a first variant, cell selection can be iteratively performed after each landing site integration. An example is shown in FIG. 11A. In a first illustrative example, each iteration (corresponding to each landing site) can include: attempting to integrate a single landing site in each of a set of cells (S100), attempting to integrate a selectable marker at the landing site (S200), and selecting cell(s) from the set of cells with the selectable marker present in the genome. In a second illustrative example, each iteration (corresponding to each landing site) can include: attempting to integrate a single landing site in each of a set of cells (S100), the landing site including a selectable marker, and selecting cell(s) from the set of cells with the selectable marker present in the genome.

Figure 11B:
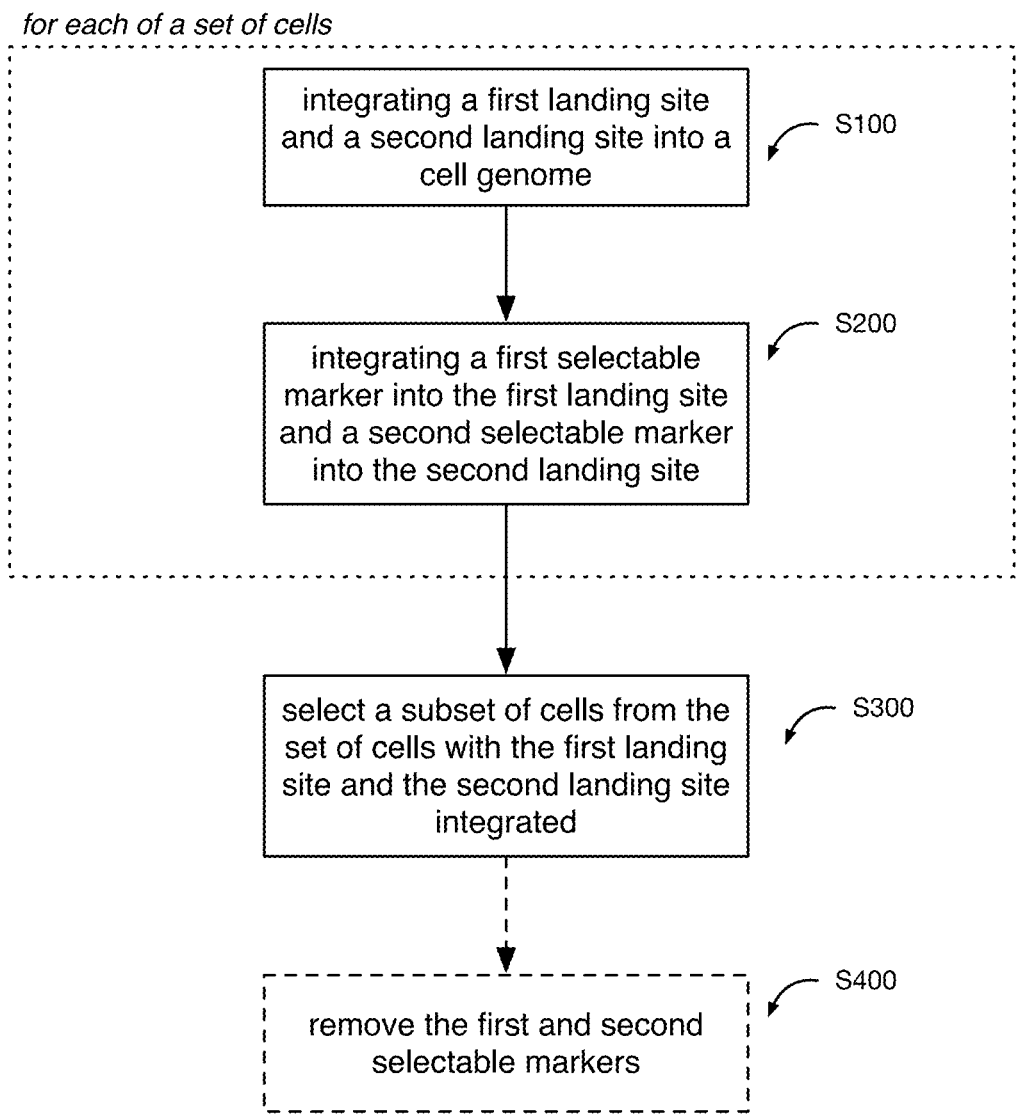

In a second variant, cell selection can be performed after integration of multiple landing sites. An example is shown in FIG. 11B. In a specific example, a set of landing sites can be integrated at each target location, wherein cell selection can be performed after all sets of landing sites are integrated and/or iteratively performed after each set of landing sites is integrated. In a first illustrative example, cell selection can include: attempting to integrate two or more landing sites in each of a set of cells (S100), attempting to integrate a selectable marker at each of the landing sites (e.g., two or more different selectable markers, one selectable marker for each landing site) (S200), and selecting cell(s) from the set of cells with all of the selectable markers present in the genome. In a second illustrative example, cell selection can include: attempting to integrate a set of landing sites (e.g., a primary landing site containing a secondary landing site, two adjacent landing sites, etc.) at a single target location in each of a set of cells (S100), attempting to integrate a selectable marker at a landing site within the set of landing sites (e.g., within a primary landing site, within a secondary landing site, etc.) (S200), and selecting cell(s) from the set of cells with the selectable marker present in the genome. In a third illustrative example, cell selection can include: attempting to integrate a first set of landing sites at a first target location and a second set of landing sites at a second target location in each of a set of cells (S100), attempting to integrate a first selectable marker at a landing site within the first set of landing sites (S200), attempting to integrate a second selectable marker at a landing site within the second set of landing sites (S200), and selecting cell(s) from the set of cells with both selectable markers present in the genome. In a fourth illustrative example, cell selection can include: attempting to integrate two or more landing sites in each of a set of cells (S100), wherein each landing site includes a different selectable marker, and selecting cell(s) from the set of cells with all selectable markers present in the genome. In a fifth illustrative example, cell selection can include: attempting to integrate a set of landing sites at a single target location in each of a set of cells (S100), wherein the set of landing sites include a selectable marker (e.g., a primary landing site includes a secondary landing site and a selectable marker), and selecting cell(s) from the set of cells with the selectable marker present in the genome. In a sixth illustrative example, cell selection can include: attempting to integrate a first set of landing sites at a first target location and a second set of landing sites at a second target location in each of a set of cells (S100), wherein the first set of landing sites include a first selectable marker and the second set of landing site includes a second selectable marker, and selecting cell(s) from the set of cells with both selectable markers present in the genome.

In a specific example, the method can include: integrating a first landing site sequence into a genome of a cell, wherein integrating the first landing site sequence includes integrating a first selectable marker bounded by a first pair of attachment site sequences inverted relative to one another; integrating a second landing site sequence into a genome of a cell, wherein integrating the second landing site sequence includes integrating a second selectable marker bounded by a second pair of attachment site sequences inverted relative to one another; performing a cell selection using the first selectable marker and the second selectable marker to select the cell; and integrating a first gene of interest and a second gene of interest, wherein integrating the first gene of interest and the second gene of interest includes replacing the first selectable marker with the first gene of interest and replacing the second selectable marker with the second gene of interest, respectively.

However, cell selection can be performed using other selection methods (e.g., without selectable markers). For example, cell selection can be performed using PCR.

However, cell selection can be otherwise performed.

4.4. Removing the Gene of Interest from the Landing Site S400.

The method can optionally include removing the gene of interest from the landing site S400, which functions to transform (e.g., return) one or more landing site attachment sites to a pre-recombination state and/or to prepare the cell for a second GOI integration (e.g., integrating a new GOI at the landing site). S400 can optionally be performed for a single landing site, for each of a set of landing sites, for a single GOI, for each of a set of GOIs, and/or any number of times. S400 can be performed after S100 (e.g., where the landing site sequence integrated in S100 includes the gene of interest), after S200, before S200 (before a second S200 iteration), after S300, and/or at any other time. In an example, the GOI is a selectable marker, wherein S400 includes removing the selectable marker after cell selection (e.g., after S300). In a specific example, each selectable marker of a set of selectable markers can be removed from its corresponding landing site (e.g., removed in a single shot, sequentially removed, etc.).

Figure 10A:
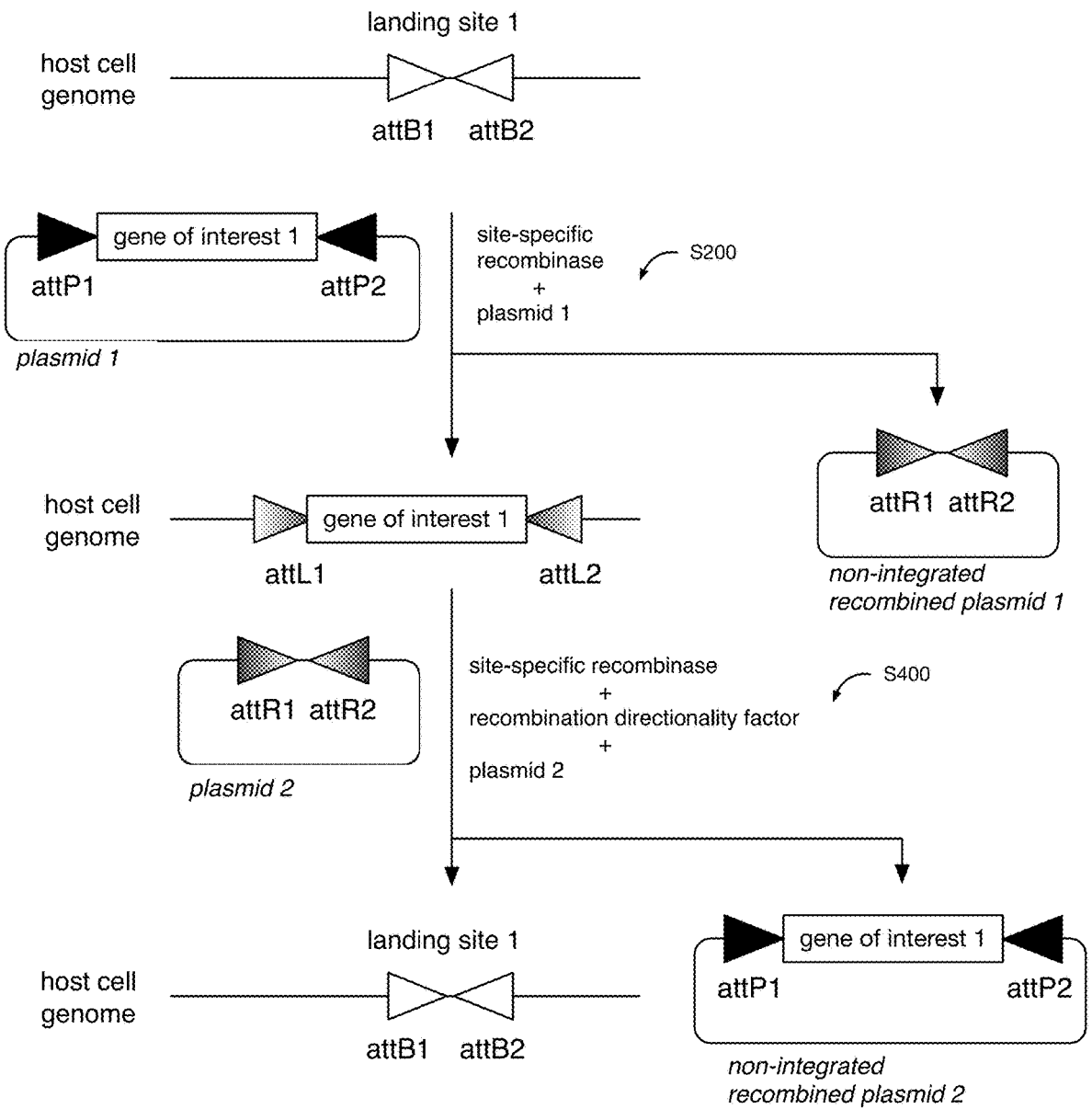
FIGS. 10A and 10B depict examples of removing a gene of interest from a landing site.
Figure 10B:
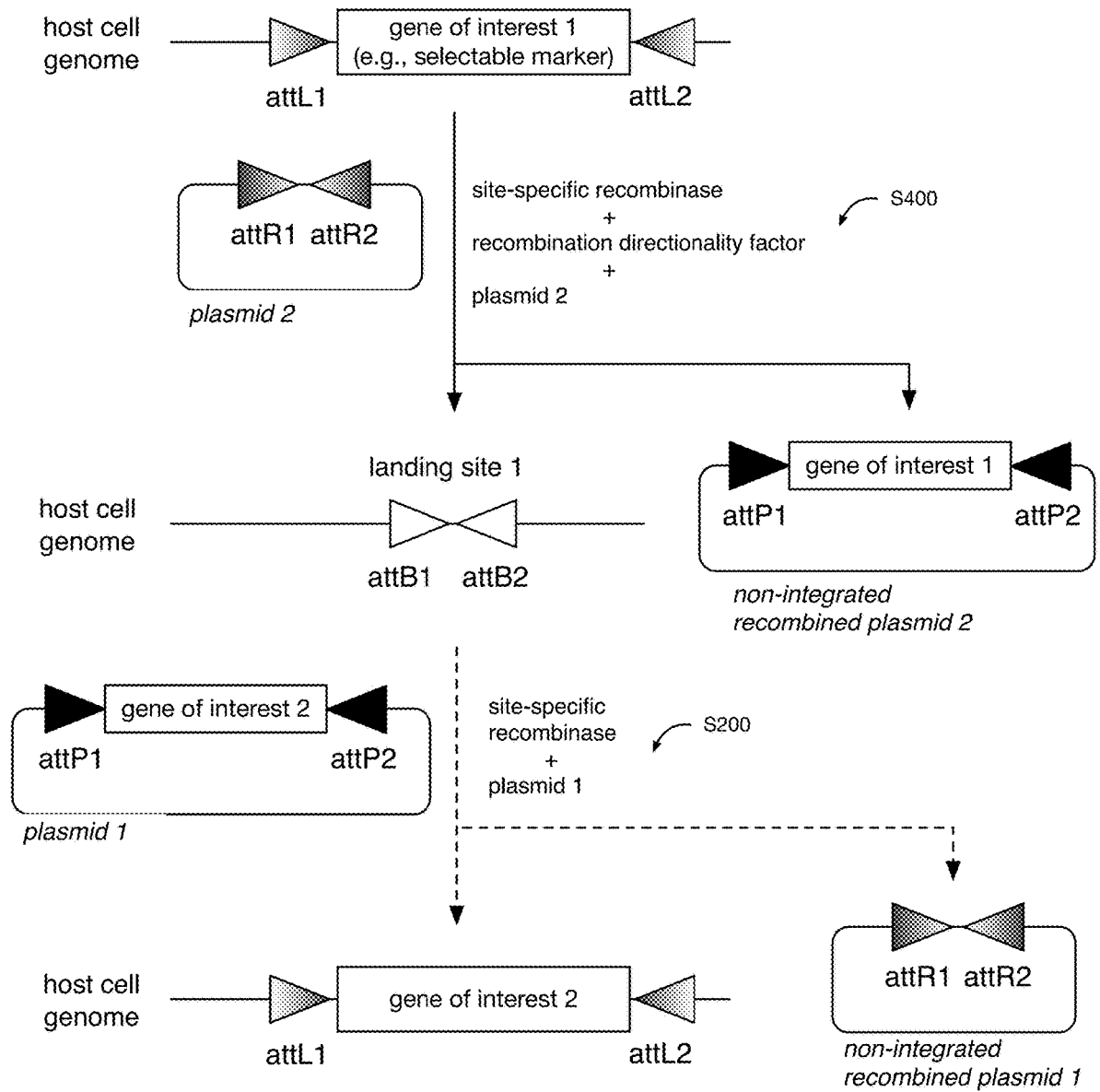

Removing the GOI from the landing site can include: using an SSR (e.g., the same SSR as used in S200 or a different SSR) and optionally a phage-encoded recombination directionality factor (RDF) to excise the GOI from the landing site. Examples are shown in FIG. 10A and FIG. 10B. In a specific example, the attachment site pair can be returned to a pre-recombination state (e.g., from attL or attR attachment sites to attP or attB attachment sites). In a first example, the landing site can include a pair of attL sites bounding the GOI, wherein S400 includes using an SSR, an RDF, and a vector containing a set of attR sites (e.g., contiguous attR sites, attR sites bounding a replacement GOI, etc.) to excise the GOI from the landing site, transforming the landing site into a pair of attB sites (e.g., contiguous attB sites, attB sites bounding the replacement GOI, etc.). In a second example, the landing site can include a pair of attB sites bounding the GOI, wherein S400 includes using an SSR and a vector containing a set of attP sites (e.g., contiguous attP sites, attP sites bounding a replacement GOI, etc.) to excise the GOI from the landing site, transforming the landing site into a pair of attL sites (e.g., contiguous attL sites, attL sites bounding the replacement GOI, etc.).

However, the GOI can be otherwise removed.

A sequence (e.g., a cell genome) can be optionally genetically engineered using all or parts of the method. For example, the sequence can be genetically engineered (e.g., genetically altered) via one or more instances of S100, S200, S300, and/or S400. In an example, a genetically engineered sequence (e.g., a genetically engineered genome of a cell) can include: one or more landing sites integrated via S100, one or more genes of interest integrated via S200, a combination thereof, and/or any other genome edits. In a specific example, the genetically engineered sequence can include one or more of SEQ ID NOS: 1-156. In some cases, the genetically engineered sequence includes a nucleotide sequence that differs by 1, 2, 3, 4, or 5 nucleotides from any of SEQ ID NOS: 1-156.

However, an engineered genome of a cell can be otherwise configured, and/or an engineered cell (e.g., genetically modified cell) can be otherwise created.

5. Specific Examples

A numbered list of specific examples of the technology described herein are provided below. A person of skill in the art will recognize that the scope of the technology is not limited to and/or by these specific examples.

Specific Example 1: A method, comprising: integrating a first landing site sequence into a first site in a genome of a cell, the first landing site sequence comprising a first pair of attachment site sequences inverted relative to one another; integrating a second landing site sequence into a second site in the genome of the cell, the second site noncontiguous with the first site, the second landing site sequence comprising a second pair of attachment site sequences inverted relative to one another; and integrating, in a single shot: a first gene of interest into the first landing site sequence; and a second gene of interest into the second landing site sequence.

Specific Example 2: The method of Specific Example 1, wherein the first site and the second site comprise different safe harbor sites.

Specific Example 3: The method of any of Specific Examples 1- or 2, wherein the first landing site sequence further comprises a third landing site sequence bounded by the first pair of attachment site sequences, the third landing site sequence comprising a third pair of attachment site sequences inverted relative to one another.

Specific Example 4: The method of Specific Example 3, wherein the first landing site sequence further comprises the first gene of interest, wherein the first gene of interest is bounded by the third landing site sequence and one of the first pair of attachment site sequences.

Specific Example 5: The method of any of Specific Examples 3 or 4, wherein the first pair of attachment site sequences comprises at least one of a pair of attB attachment site sequences or a pair of attP attachment site sequences, and wherein the third pair of attachment site sequences comprises one of a pair of attL attachment site sequences or a pair of attR attachment site sequences.

Specific Example 6: The method of any of Specific Examples 3-5, wherein integrating the first landing site sequence comprises: transfecting the cell with a vector containing the third pair of attachment site sequences bounded by the first pair of attachment site sequences.

Specific Example 7: The method of any of Specific Examples 1-6, wherein integrating the first landing site sequence comprises integrating a first selectable marker bounded by the first pair of attachment site sequences, wherein integrating the second landing site sequence comprises integrating a second selectable marker bounded by the second pair of attachment site sequences; the method further comprising performing a cell selection using the first selectable marker and the second selectable marker to select the cell, wherein integrating the first gene of interest and the second gene of interest comprises replacing the first selectable marker with the first gene of interest and replacing the second selectable marker with the second gene of interest, respectively.

Specific Example 8: The method of any of Specific Examples 1-7, wherein integrating the first gene of interest and the second gene of interest comprises: transfecting the cell with a vector containing the first gene of interest and the second gene of interest.

Specific Example 9: The method of any of Specific Examples 1-8, wherein the first landing site sequence and the second landing site sequence are integrated in a single shot by transfecting the cell with a vector containing the first landing site sequence and the second landing site sequence.

Specific Example 10: The method of any of Specific Examples 1-9, wherein the first gene of interest and the second gene of interest are integrated using a site-specific recombinase.

Specific Example 11: A genetically engineered cell, comprising: an engineered genome, comprising: a first landing site sequence comprising a first attachment site sequence and a second attachment site sequence, wherein the first attachment site sequence is inverted relative to the second attachment site sequence; and a second landing site sequence bounded by the first attachment site sequence and the second attachment site sequence, the second landing site sequence comprising a third attachment site sequence and a fourth attachment site sequence, wherein the third attachment site sequence is inverted relative to the fourth attachment site sequence.

Specific Example 12: The genetically engineered cell of Specific Example 11, wherein the first landing site sequence and the second landing site sequence are simultaneously integrated into a genome of the genetically engineered cell.

Specific Example 13: The genetically engineered cell of any of Specific Examples 11 or 12, wherein the engineered genome further comprises: a first gene of interest bounded by the first attachment site sequence and the third attachment site sequence; and a second gene of interest bounded by the third attachment site sequence and the fourth attachment site sequence.

Specific Example 14: The genetically engineered cell of Specific Example 13, wherein the first gene of interest comprises at least one of: a selectable marker, an opsin, a killswitch, or a transcription factor.

Specific Example 15: The genetically engineered cell of any of Specific Examples 11-14, wherein the engineered genome further comprises: a third landing site sequence noncontiguous with the first landing site sequence, the third landing site sequence comprising a fifth attachment site sequence and a sixth attachment site sequence, wherein the fifth attachment site sequence is inverted relative to the sixth first attachment site sequence.

Specific Example 16: The genetically engineered cell of Specific Example 15, wherein the first landing site sequence is located at least 10000 base pairs from the third landing site sequence in the engineered genome.

Specific Example 17: The genetically engineered cell of any of Specific Examples 11-16, wherein each of the first, second, third, and fourth attachment site sequences comprise unique sequences.

Specific Example 18: The genetically engineered cell of any of Specific Examples 11-17, wherein each of the first, second, third, and fourth attachment site sequences are not compatible with one another.

Specific Example 19: The genetically engineered cell of any of Specific Examples 11-18, wherein each attachment site sequence comprises at least one of: attB, attP, attL, or attR attachment site sequences.

Specific Example 20: The genetically engineered cell of any of Specific Examples 11-19, wherein the genetically engineered cell comprises a genetically engineered human induced pluripotent stem cell.

Specific Example 21: The genetically engineered cell of any of Specific Examples 11-20, wherein the genetically engineered cell comprises a genetically engineered hypoimmunogenic cell.

Specific Example 22: The genetically engineered cell of any of Specific Examples 11-21, wherein the engineered genome further comprises: a third landing site bounded by the third attachment site sequence and a fourth attachment site sequence.

Specific Example 23: The genetically engineered cell of any of Specific Examples 11-22, wherein the engineered genome further comprises: a third landing site bounded by the first attachment site sequence and the third attachment site sequence.

Specific Example 24: The genetically engineered cell of any of Specific Examples 11-23, wherein the engineered genome further comprises: a third landing site bounded by the fourth attachment site sequence and the second attachment site sequence.

Specific Example 25: A method for producing (e.g., genetically engineering) the genetically engineered cell of any of Specific Examples 11-24.

Specific Example 26: A genetically engineered cell produced (e.g., genetically engineered) by any of Specific Examples 1-10.

As used herein, "substantially" or other words of approximation (e.g., "about," "approximately," etc.) can be within a predetermined error threshold or tolerance of a metric, component, or other reference (e.g., within +/−0.001%, +/−0.01%, +/−0.1%, +/−1%, +/−2%, +/−5%, +/−10%, +/−15%, +/−20%, +/−30%, any range or value therein, of a reference).

All references cited herein are incorporated by reference in their entirety, except to the extent that the incorporated material is inconsistent with the express disclosure herein, in which case the language in this disclosure controls.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. An in vitro method of genetically modifying a cell in multiple loci of the genome, the method comprising:
   (i) transfecting the cell with:
      (a) a first donor vector comprising a first primary landing site sequence and encoding a first gRNA comprising a targeting sequence to a first safe harbor site;
      (b) a second donor vector comprising a second primary landing site sequence and encoding a second gRNA comprising a targeting sequence to a second safe harbor site; and
      (c) a CRISPR Cas 9 nuclease;
      wherein the first primary landing site sequence comprises a first pair of site-specific recombinase attachment site sequences flanking a secondary landing site sequence comprising a second pair of site-specific recombinase attachment site sequences, wherein the first pair of site-specific recombinase attachment site sequences are inverted relative to each other, wherein the second primary landing site sequence comprises a third pair of site-specific recombinase attachment site sequences inverted relative to each other, and wherein the first primary landing site sequence integrates into the first safe harbor site in the genome of the cell and the second primary landing site sequence into the second safe harbor site in the genome of the cell; and
   (ii) transfecting the cell with:
      (a) a third vector comprising a first gene of interest flanked by a fourth pair of site-specific recombinase attachment sites;
      (b) a fourth vector comprising a second gene of interest flanked by a fifth the pair of site-specific recombinase attachment sites; and
      (c) a site-specific recombinase enzyme;
      wherein the fourth pair of site-specific recombinase attachment sites are compatible with the second pair of site-specific recombinase attachment sites, and wherein the first gene of interest integrates into the site of the second pair of site-specific recombinase attachment sites of the secondary landing site sequence; and
      wherein the fifth pair of site-specific recombinase attachment sites are compatible with the third pair of site-specific recombinase attachment sites, and wherein the second gene of interest integrates into the site of the second site-specific recombinase attachment sites of the second primary landing site sequence.

2. The method of claim 1, wherein the first primary landing site sequence further comprises a third gene of interest, wherein the third gene of interest is bounded by the secondary landing site sequence and one of the first pair of attachment site sequences.

3. The method of claim 1, wherein the second pair of attachment site sequences comprises one of a pair of attB attachment site sequences or a pair of attP attachment site sequences, and wherein the first pair of attachment site sequences comprises one of a pair of attL attachment site sequences or a pair of attR attachment site sequences.

4. The method of claim 1, wherein the cell is transfected with the third vector, the fourth vector, and the site-specific recombinase enzyme in a single shot.

5. The method of claim 1, wherein at least one of the first gene of interest or the second gene of interest comprises an opsin gene.

6. The method of claim 1, wherein at least one of the first gene of interest or the second gene of interest comprises a transcription factor gene.

7. The method of claim 1, wherein at least one of the first gene of interest or the second gene of interest comprises a selectable marker gene.

* * * * *